US011241573B2

(12) United States Patent
John et al.

(10) Patent No.: US 11,241,573 B2
(45) Date of Patent: Feb. 8, 2022

(54) PERCUTANEOUS AND TRANSCUTANEOUS PERIPHERAL NEUROMODULATION

(71) Applicant: EBT MEDICAL, INC., Toronto (CA)

(72) Inventors: Michael Sasha John, Larchmont, NY (US); Paul B. Yoo, Toronto (CA)

(73) Assignee: EBT Medical, Inc., Toronto (CA)

(*) Notice: Subject to any disclaimer, the term of this patent is extended or adjusted under 35 U.S.C. 154(b) by 0 days.

(21) Appl. No.: 16/193,894

(22) Filed: Nov. 16, 2018

(65) Prior Publication Data

US 2019/0143097 A1    May 16, 2019

Related U.S. Application Data

(60) Provisional application No. 62/587,116, filed on Nov. 16, 2017.

(51) Int. Cl.
| | | |
|---|---|---|
| *A61N 1/05* | (2006.01) | |
| *A61N 1/04* | (2006.01) | |
| *A61N 1/36* | (2006.01) | |
| *A61N 2/00* | (2006.01) | |
| *A61M 5/142* | (2006.01) | |
| *A61H 3/00* | (2006.01) | |

(52) U.S. Cl.
CPC ......... *A61N 1/0456* (2013.01); *A61N 1/3603* (2017.08); *A61N 1/36007* (2013.01); *A61N 1/36017* (2013.01); *A61N 2/006* (2013.01); *A61H 3/00* (2013.01); *A61M 5/142* (2013.01); *A61N 1/0484* (2013.01); *A61N 1/0502* (2013.01); *A61N 1/3606* (2013.01)

(58) Field of Classification Search
CPC .................................................. A61N 1/0502
See application file for complete search history.

(56) References Cited

U.S. PATENT DOCUMENTS

| | | | | |
|---|---|---|---|---|
| 2001/0021869 | A1* | 9/2001 | Bishay | A61N 1/0551 607/116 |
| 2004/0147995 | A1* | 7/2004 | Miazga | A61N 1/0551 607/142 |
| 2004/0147996 | A1* | 7/2004 | Miazga | A61N 1/0551 607/142 |
| 2006/0206164 | A1* | 9/2006 | Gavronsky | A61H 39/002 607/46 |
| 2008/0154334 | A1* | 6/2008 | Gavronsky | A61N 1/0558 607/46 |
| 2011/0015469 | A1* | 1/2011 | Walter | A61B 5/01 600/27 |
| 2016/0113678 | A1* | 4/2016 | Roychowdhury | A61H 39/08 606/129 |

* cited by examiner

*Primary Examiner* — Allen Porter
(74) *Attorney, Agent, or Firm* — Rosenberg, Klein & Lee

(57) ABSTRACT

Improved systems are disclosed for providing advantages during stimulation of peripheral nerves using transcutaneous, percutaneous, and implantable stimulators. Percutaneous stimulation is improved by accessories that guide the angel and depth of injection to allow for easy and controlled needle injection. Transcutaneous stimulation is improved using pressure to improve nerve recruitment. Systems and methods are disclosed for providing nerve stimulation of a patient to treat medical disorders and conditions within a single user or multiple user environments such as assisted living centers.

20 Claims, 15 Drawing Sheets

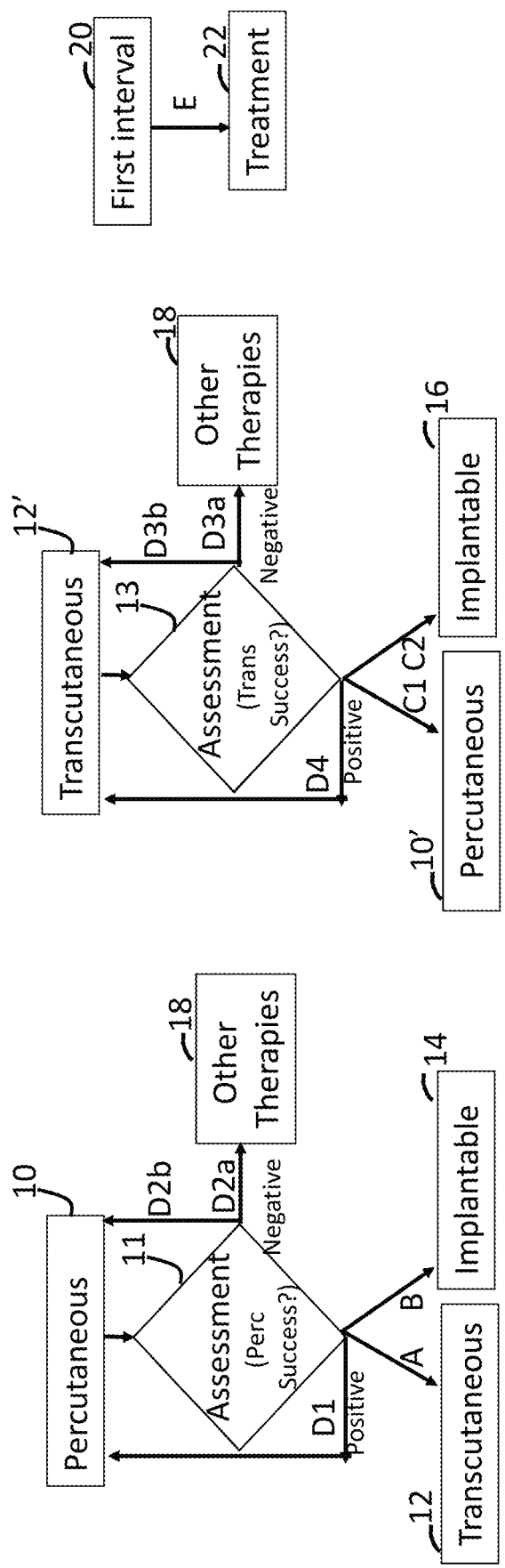

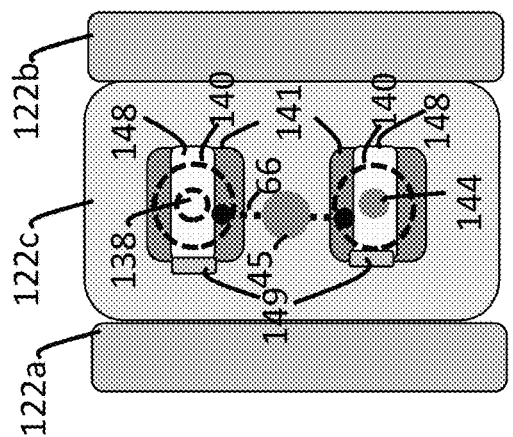
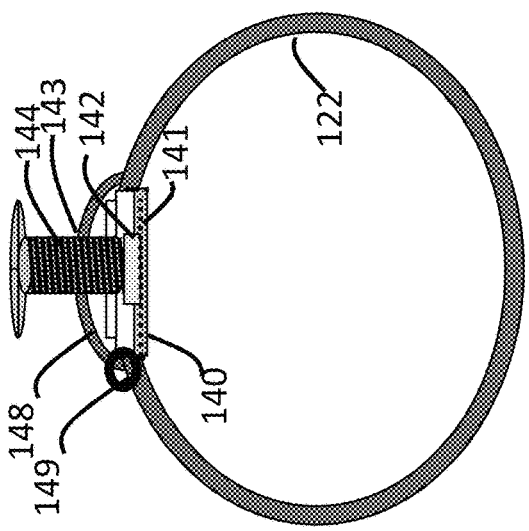
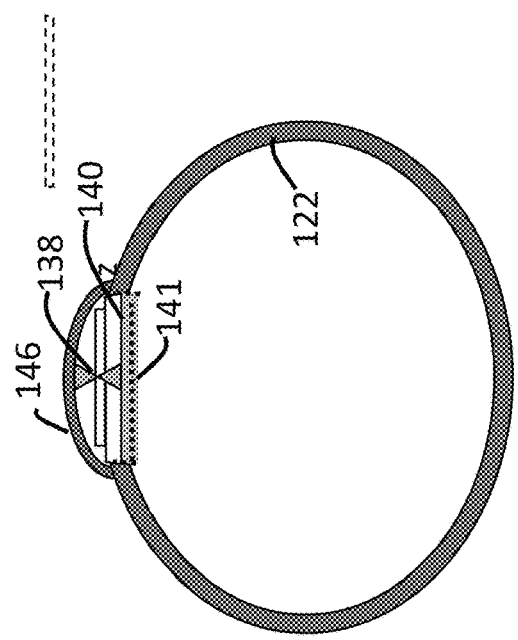
FIG. 4E
FIG. 4F
FIG. 4G

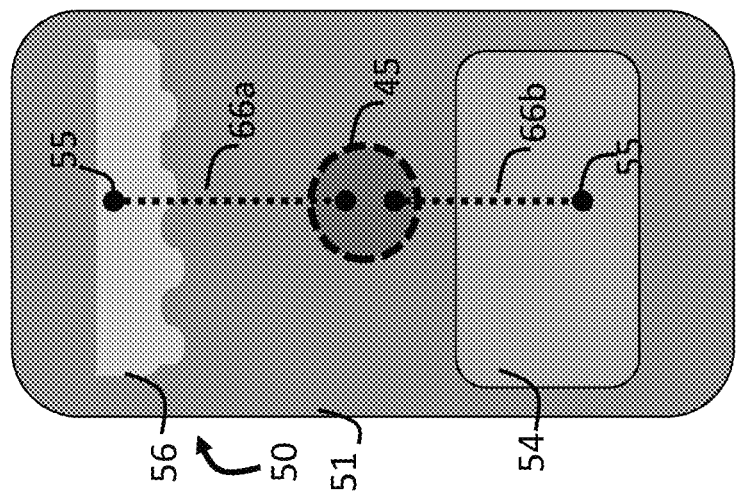
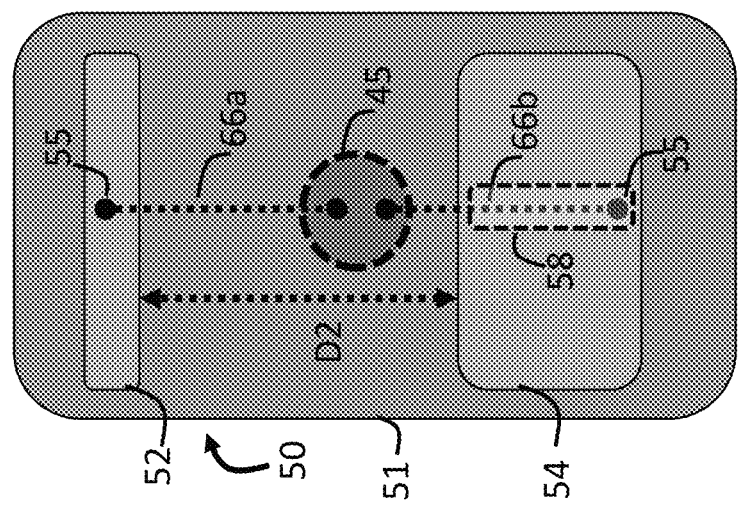
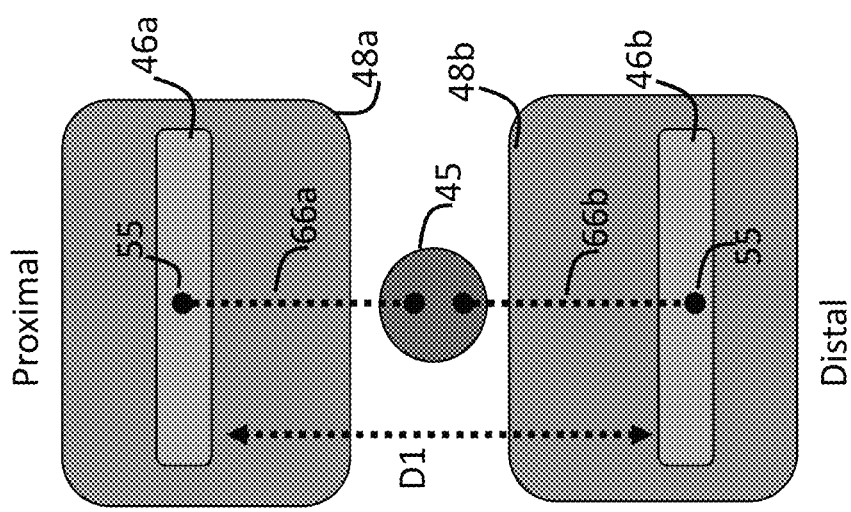
FIG. 5C
FIG. 5B
FIG. 5A

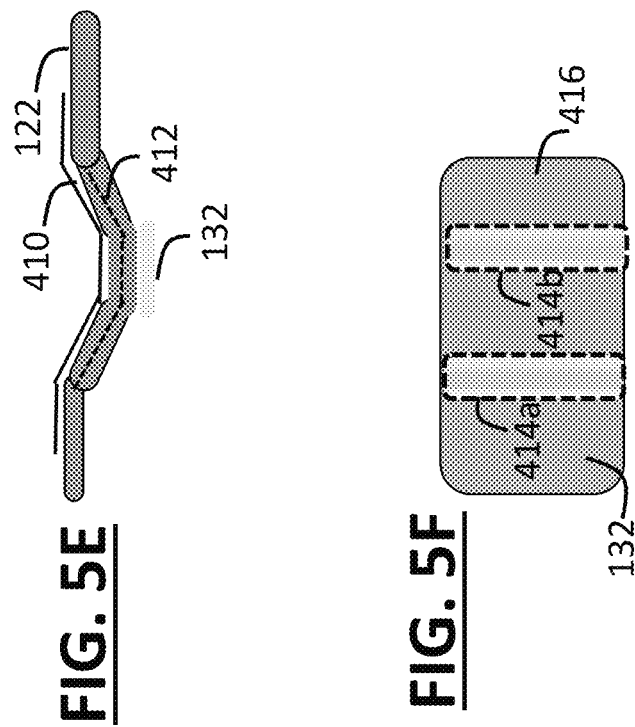
FIG. 5E
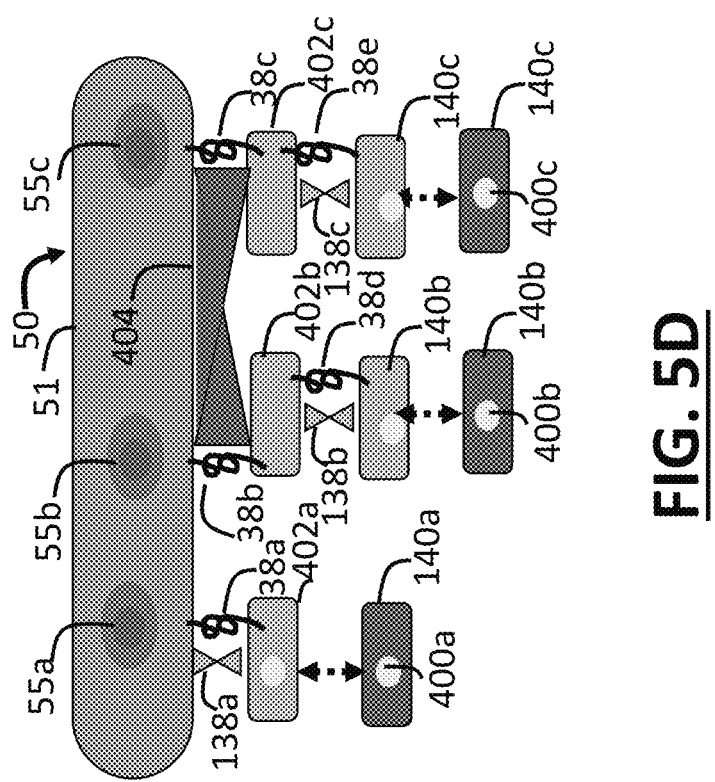
FIG. 5F
FIG. 5D

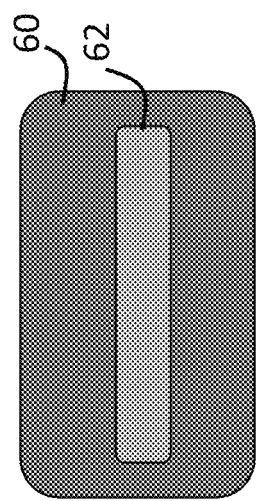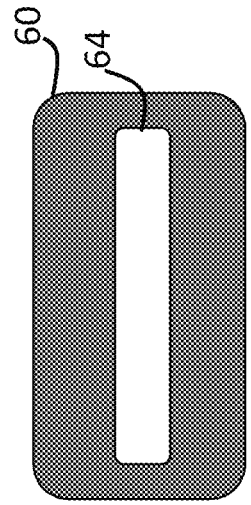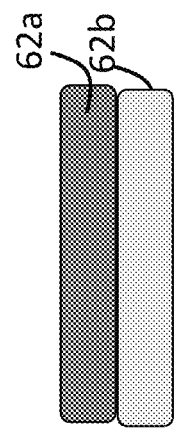
FIG. 6A
FIG. 6B
FIG. 6C

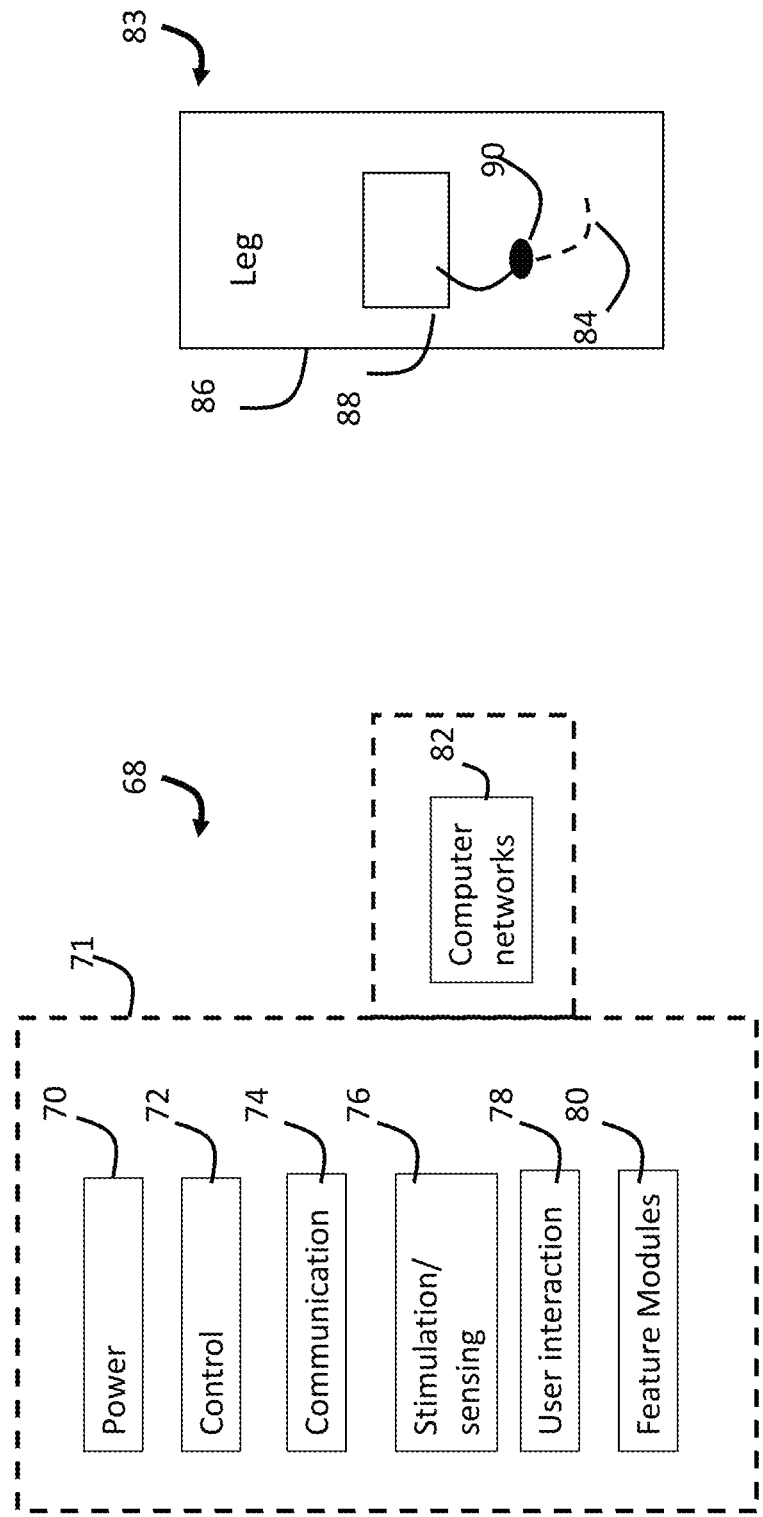

| Room # | Name | Next Round | Toileting | Dur | Provider | Fall Risk | OOB Status | Next Stim | Next Med | Med Provider | Diuretic | # voids | Trending | OAB Status | Pads | Wet/Dry | UTI | Alarms/Alerts |
|---|---|---|---|---|---|---|---|---|---|---|---|---|---|---|---|---|---|---|
| 2000 | Roberts | 13:00 | Scheduled | 10 | Murphy | H | In Bed | 13:20 | 13:20 | BA | 1 | 4(e9)(n1) | 0 | Urge | 2 | 10% | Pos | 0/2 |
| 2001 | Walker | 14:00 | Prompted | 5 | Murphy | M | Sleeping | 2D | 14:15 | BR | 2 | 3(e7)(n2) | +1 | Urge | 1 | 0% | Neg | 0/0 |
| 2002 | Montalba | 16:00 | <><> | <><> | <><> | L | In Room | 1D | 16:20 | BH | 2 | 3(e7)(n2) | -2 | Mixed | 2 | 0% | Neg | 0/2 |
| 2003 | Englander | 16:00 | Scheduled | 20 | Murphy | <><> | Walking | <><> | <><> | <><> | 1 | 3(e7)(n2) | 0 | <><> | 0 | 0% | Neg | 0/0 |
| 2004 | Carlton | 17:00 | Scheduled | 5 | Murphy | L | Activity | 17:10 | 17:10 | BB | 4 | 3(e7)(n2) | 0 | Stress | 3 | 30% | Recur | 0/2 |
| 2005 | Mapps | 17:30 | Prompted | 10 | Vonces | L | Activity | 14:15 | 17:50 | <><> | 2 | 3(e7)(n2) | -1 | Mixed | 2 | 10% | Neg | 0/0 |

FIG. 11

PERCUTANEOUS AND TRANSCUTANEOUS PERIPHERAL NEUROMODULATION

CROSS-REFERENCE TO RELATED APPLICATIONS

This application claims priority of provisional application Ser. No. 62/587,116, filed 16 Nov. 2017.

FIELD

The invention in in the field of stimulating tissue to modulate biological activity.

BACKGROUND

Pelvic floor disorders such as overactive bladder (OAB) have been successfully treated with drugs, stimulation provided at the level of the spine (sacral nerve), and peripheral stimulation of sites such as the posterior tibial nerve (PTN). Pelvic floor disorders include, for example, bladder and bowel disorders affecting symptoms such as urge, frequency and incontinence. The inventors have recently done preclinical and clinical work that supports that the saphenous nerve (SAFN) can also provide therapy in the treatment of OAB. Stimulation of the SAFN, and other peripheral nerves, may be effective in treatment of other disorders such as hypertension, and autonomic nervous system disorders or unwanted states. Modulation of the SAFN can be combined with stimulation of other peripheral nerves in the leg such as the PTN, sural nerve, and other peripheral nerves of the body to provide treatment of disorders and symptoms.

Transcutaneous peripheral stimulation poses challenges such as successful recruitment of a target nerve which can be hampered by thick cutaneous tissue, dry or damaged skin, edema, characteristics of intervening tissue, anatomical variability of nerve location, and other issues. It would be useful to have improved systems (designs and components) and methods for enabling or facilitating successful nerve stimulation in the treatment or modulation of the state of an organism. Enabling clinic-based or home-based treatment using peripheral nerve stimulation (provided by a patient or caregiver rather than a trained medical staff member) with improved transcutaneous and percutaneous stimulation delivery designs may offer greater convenience and less side effects than treatments requiring clinic visits or drug therapy.

Healthcare Risk Control (HRC) includes a focus on communication, patient safety, and patient experience, and their interrelationship. Communication of information such as voiding history, bladder and bowel health status, and upcoming scheduled events improves "patient handoff" and continuity of care as staff shifts begin and end. Communication errors contribute to 65% of reported sentinel events (unanticipated events, not related to the natural course of the patient's illness, resulting in physical or psychological injury to a patient).

Hospital Consumer Assessment of Healthcare Providers and Systems (HCAHPS) scores are now important to a portion of federal reimbursement. Facilities must promote and validate patient satisfaction. Improvement in scores is increased by providing information that allows patients to anticipate scheduled activities and care. A display of medical-related information at a nursing station, in the patient's room (and even just outside of the patient's room so medical staff may review prior to entering the room), improves resource management and care. Better care can improve readmission rates, duration of hospital stay, decrease comorbidities, and increase level of reimbursement.

About half of patients in managed healthcare facilities suffer from OAB/incontinence. Many of the falls experienced by residents in facilities are related to bathroom activities. Falls are the third most common cause of unintentional injury and death across all age groups.

SUMMARY

The invention includes novel systems, methods, and protocols for treatment that provide improved, easier, and more convenient therapy for medical disorders and symptoms. Disclosed systems and methods include at-home and clinic-based percutaneous stimulation, new electrode designs and protocols that can improve stimulation provided by transcutaneous nerve stimulation (TNS) using electrical, magnetic or other energy, and/or also provided by implantable components and devices. The methods and system disclosed herein for transcutaneous stimulation can also be realized using implantable, or mixed embodiments including both external and implanted components such as an implanted stimulator that is powered externally.

Embodiments disclosed using percutaneous, transcutaneous, or implantable stimulation devices can be combined (at the same or different times) or substituted. A first mode of stimulation may inform successful application of a second type of stimulation. For example, during screening periods and procedures, sites and stimulation parameters determined to be successful using percutaneous stimulation may allow for correct positioning of implantable stimulators (e.g., the candidate sites which show the lowest threshold for nerve recruitment may be preferential as site of implant).

When stimulating certain nerves (e.g., the PTN), transcutaneous stimulation may produce less robust treatment response than percutaneous stimulation. Without being limited by theory, broader fields provided by TENS stimulation patches or "electrode pads" may result in decreased treatment response compared to needle stimulators. Reducing the size of TENS pad conductive surface may provide a more focused field. Although TENS electrodes used for stimulating muscle typically have square or rectangular shapes (e.g., 1.5×1.5 inches), a narrower electrode shape (or electrically conductive element) may provide benefits when stimulating nerves (with a more focused field). Small pad size and using at least two electrode pads of different sizes can provide for increased current density and decreased area of nerve activation.

An object of the invention is to provide a percutaneous accessory device that allows stimulation to occur without a trained medical staff inserting a stimulation needle.

An object of the invention is to provide improved systems for treating certain patients who may encounter difficulty in providing stimulation and successful recruitment of a target nerve such as a nerve in the leg. This can facilitate therapy otherwise impeded by conditions such as edema which cause swelling of tissue and fluid build-up near the target nerve, or due to patients having excessive skin, fat, or other intervening tissue between a conventional transcutaneous stimulation pad and a nerve target.

An object of the invention is to provide a system for data collection, scoring, treatment, management, and reporting related to bladder and bowel health that allows hospitals to improve the patient experience and decrease caretaker time and effort. Providing information about urination and defecation activities and status to patients, caretakers, and medical staff allows correct management and intervention leading to improved patient outcome. Since patients regularly empty bladders and bowels, providing information about management and treatment related to voiding can improve care.

The various other advantages and problems in the prior art which are overcome by the inventions disclosed herein will now be disclosed in the figures, detailed description, and claims.

SUMMARY OF FIGURES

FIGS. 1A and 1B show methods steps for providing patient stimulation and assessment at different points along a patient treatment path.

FIG. 2 shows a method having a first interval with assessment that informs stimulation provided during a second interval having a selected stimulation type and protocol.

FIGS. 4E, 4F and 4G show embodiments of wearable neurostimulators having biased TENS pads for improved nerve recruitment.

FIGS. 5A, 5B, and 5C show embodiments of array and stimulator electrodes.

FIG. 5D shows example embodiments of biasing members disposed in an electrode array.

FIG. 5E shows an embodiments of exoskeleton and endoskeleton biasing members.

FIG. 5F shows an embodiment of a conductive pad used for transcutaneous stimulation or sensing having two raised portions that are offset from a flat bottom surface.

FIGS. 6A, 6B and 6C show embodiments of implantable passive component (IPC) designs.

FIG. 7 shows an illustrative embodiment of a device and system for providing therapy to patients which interfaces with computer networks.

FIG. 8 shows a percutaneous stimulator providing stimulation and using a TENS electrode for a return path.

FIG. 11 shows an example of an interactive digital display of the patient management platform (PMP) system which is suitable for operation by a staff member at a nurse station.

DETAILED DESCRIPTION

Figure 3B:
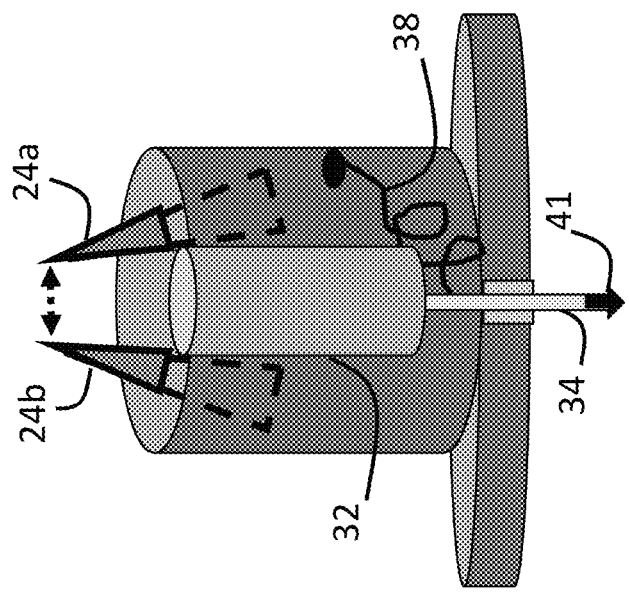
FIGS. 3A and 3B show an example embodiment of a percutaneous stimulation accessory in an undeployed and deployed state, respectively.

FIGS. 1A and 1B show steps that may occur along a patient's treatment pathway starting with assessment of induction stimulation and evaluation assessment criteria using stimulation-related changes in symptoms or other measures. In embodiments, the methods of FIGS. 1A and 1B serve to provide screening that occurs prior to implantation of a neurostimulator. Assessment which includes at least one stimulation induced change in symptoms, behavior, neural or muscle activity, or other measure can be used to determine whether a patient may be a good candidate for treatment by one or more implanted neurostimulators, with associated limitations. Although a peripheral neurostimulator may simply be implanted in a patient without such assessment, due to the invasive and costly procedure, prior assessment according to these methods allows for a well-informed selection of a candidate patient who has greater chance for receiving treatment benefit. FIG. 2 shows that a first assessment or screening interval 20 contingently leads to a second interval during which the same or different treatment type or protocol is provided 22. In embodiments, stimulation protocols provided in a first interval, can provide treatment in the second interval when provided alone, or in combination, or sequentially with additional steps and protocols. In some therapy paths the treatment simply starts when a patient receives an implantable device for providing therapy 14. However, when a first interval is used 20 to inform treatment delivered later, then therapy 22 therapy with an implanted device may be augmented by additional stimulation provided by TENS or percutaneous therapy, since is determined that the scheduled stimulation provided by an implanted device is not sufficiently effective.

As shown in FIG. 1A, in an embodiment the patient undergoes assessment with percutaneous stimulation 10 of a nerve. For example, in step 10 assessment occurs for SAFN stimulation in the treatment of a pelvic floor disorder such as OAB. The step of percutaneous stimulation 10 has an induction period such as 4 to 12 weeks. A schedule of weekly clinic visits over a 12-week interval is commonly used in percutaneous PTN induction. If following the screening interval an assessment in step 11 leads to a positive outcome and the patient demonstrates a benefit such as decreased symptom severity, then treatment can continue along path D1 with maintenance treatment (at the same or less frequent rate of treatment). Treatment flow along path D1 includes the step of continuing with percutaneous therapy which may entail providing therapy in the clinic or in an at-home setting using percutaneous accessory device disclosed herein. Alternatively, if the assessment done percutaneously in step 10, meets one or more screening criteria successfully in assessment step 11 then the screening result is positive (i.e., successful) and the patient may progress along treatment path "A" to receive TENS treatment 12, or path "B" to receive treatment with an implantable device 14. Additional variables that are assessed as part of the assessment step 11 may determine the which step occurs afterwards (e.g. step 10 or 11). The first interval of stimulation 20 leads to a second interval of treatment 22 that is adjusted contingently upon whether the patient meets at least one percutaneous screening criterion.

Successful candidacy for treatment with an implantable device may use a screening assessment interval of longer than 12 weeks in step 10 to determine if benefit continues to be maintained over a longer interval. The implanted device treatment 14 may occur in a peripheral location such as the leg to stimulate at least one nerve that was assessed with the percutaneous stimulation 10. However, the nerve or nerve location used during assessment and can be the same or different as that used during treatment.

In embodiments, treatment path (e.g., from 10 to either 12 or 14) is contingently selected in step 11 based upon assessment of stimulation provided in steps 10 (or 11 of FIG. 1B) and also based upon patient, doctor, or caretaker preference and/or at least one of the following (with respect to one or more symptoms): symptom severity, symptom type, symptom timing, symptom size, change from a pre-treatment baseline, change in symptoms due to combined stimulation and drug treatment, or other measurements obtained during the induction/assessment period. Symptoms are measured by scoring of bladder diaries, subjective surveys/reports, and quality of life surveys.

In embodiments, the results of the assessment step 11 cause the treatment path to be adjusted based upon an assessment of a demographic, biological, physiological, or anatomical characteristic, or baseline or change in nerve/muscle activity including evoked activity, response to drug treatment, and concurrent drug therapy (past, present, or planned). The treatment path and stimulation parameters can be adjusted contingently based upon patient response to therapy as quantified by one or more "change scores" reflecting a change in an instrument such as a quality of life survey (e.g. OAB-Q), 4-day bladder diary, or sets of questions related to patient behavior across two or more datasets. Measurements of therapy benefit can assess not only improvements in symptoms but also normalization or change in patient behavior. For example, if a patient's voiding activity remains about the same, but fluid consumption increases from 1 to 3 cups of coffee a day, then benefit may be reflected by ability to increase fluid intake without a worsening of symptoms. Further, ability to consume diuretics such as coffee may be scored higher than, for example, water, when a weighted score is calculated to assess benefit.

In embodiments, measurements are obtained both at the start and end of the assessment period to calculate at least one symptom change score which is evaluated during the assessment step 11 and yields either a positive or negative outcome depending upon at least one treatment criterion. Returning to FIG. 1A, induction stimulation is provided 10, if the assessment in step 11 does not lead to a positive outcome then the patient may travel along treatment path D2*a* which leads to a step of providing alternative therapies such as drug therapy, treatment with Botox, more invasive options such as surgery, or other intervention. In an embodiment, the alternative therapy is combined with an electrical stimulation therapy which continues. Alternatively, lack of a positive outcome in step 11 leads along path D2*b*, which includes providing another assessment interval after adjusting the assessment protocol such as, for example, increasing the number of stimulation sessions per week, adjusting the electrode position, nerve being stimulated, stimulation parameters, or number of sites which are stimulated, etc. On advantage of using percutaneous induction during an assessment period to determine which subjects may benefit from transcutaneous stimulation is that if patients do not subsequently respond to transcutaneous treatment, then the problem may be the ability of the transcutaneous stimulation signal to provide successful nerve (e.g., SAFN) recruitment.

In an embodiment, assessment of stimulation and contingent selection of a treatment path is done in step 11 (by assessment which includes using at least one treatment criterion) using a shorter interval that includes one or two clinic visits rather than spanning weeks or months. The assessment is done for disorders such as pelvic floor disorders (e.g., OAB, pelvic pain, altered sexual function, changes in urinary or fecal voiding which causes discomfort to the patient, etc.), or other disorders. For example, assessment occurs during or after 1 or more treatment sessions and assessing electrical measures such as nerve or muscle activity sensed by an implanted or external sensor. Other measures may also be used in the assessment of stimulation related changes for selected disorders, such as a Galvanic skin response (GSR), pupil dilation, blood pressure, heart rate, heart rate variability, or measure related to either sympathetic or parasympathetic activity, or combination measure reflecting a state of the autonomic nervous system. For example, in the disorder of hypertension, assessment of stimulation changes in blood pressure may be used in selecting treatment path between electrical and drug therapy. In step 11, measures can be assessed by algorithm, user, or physician. The outcome of step 11 is used to select treatment path and adjust a therapy protocol in an open loop, closed loop, or semi-closed loop manner (e.g., the system provides feedback using an algorithm but the actual change in therapy is done manually).

In an embodiment, assessment of treatment response in step 11 may be done in relation to treatment parameters such as electrode position, stimulation parameters, and target nerve(s). The assessment includes evaluation using measures of nerve recruitment including, for example, subjective sensations reported by the patient or objective measures of evoked activity. Objective measures include, for example, electrical measurements such as somatosensory evoked potentials, compound nerve action potentials, and other types of evoked nerve activity, as is well known.

In embodiments, the evaluation of treatment parameters, treatment response, and one or more patient inclusion/exclusion criteria are assessed during a single screening visit. For example, during the first visit which occurs as part of step 12 the patient (e.g., a diabetic who suffers from neuropathy) is unable to report a sensation that confirms successfully nerve recruitment. If this is defined as a screening criterion then when this is assessed in step 13 the patient may be rejected as a candidate for a treatment path such as transcutaneous SAFN stimulation. For some patients, the rejection is medically beneficial because the patient would not be able to determine if the TENS pads positions and stimulation amplitude was high enough to recruit the SAFN. Alternatively, rather than rejecting the patient, step 13 can additionally, or alternatively, include measurement and assessment of nerve/neural measures (e.g., evoked potentials data) sensed during screening of a patient, candidate nerve site, or stimulation parameters. The screening stimulation and assessment determine what treatment protocols may be suitable for a patient.

FIG. 1B shows assessment that starts with transcutaneous stimulation. In embodiments, the assessment step 13 occurs for evaluation of transcutaneous stimulation 12'. In an example, transcutaneous stimulation 12' includes both an induction phase and a maintenance phase. The maintenance includes a less frequent therapy schedule (e.g. 1× every 3-4 weeks) or shorter stimulation session duration (e.g. 30 instead of 60 minutes) to determine if a lower dosage is adequate to maintain benefit see during induction. The outcomes of both the induction and maintenance are assessed 13 to select an appropriate therapy path. In other words, steps 12' and 13 can include maintenance therapy with repeated evaluation as part of the assessment that determines the treatment path and protocol. For example, if during maintenance the frequent treatment (e.g., one treatment every 3-4 weeks) is assessed as sufficient to yield a positive assessment result, then the patient may be assigned to path "D4" for TENS treatment. The therapy occurs infrequently and so the patient can provide stimulation at home. Alternatively, in the case of a positive outcome with good symptom relief the patient is found to be a suitable candidate for an implantable treatment option therapy 16 moving along path "C2". An implantable device having a battery may be limited in the schedule and duration due to power considerations, but can increase patient compliance, comfort, and convenience. The assessment that occurs in step 13 may include assessment of these additional considerations. An additional treatment path can cause a patient to move along path "C1" where percutaneous stimulation 10' is used and relies on one more percutaneous devices disclosed herein. A negative outcome (reflecting insufficient symptom relief) results in path "D3a" or "D3b". In D3a, an alternative therapy option is selected. In treatment path D3b transcutaneous stimulation is selected, but the stimulation protocol, parameters, or dose (schedule or duration) is adjusted (e.g., dose is increased). Alternative treatment paradigms and treatment path permutations are also possible.

In an embodiment the assessment step occurs during a first interval (or set of intervals) in step 12' includes an induction phase of 8-12 weeks with stimulation occurring at a rate of 2-3× per week. In step 13, if the assessment leads to a negative outcome, then the method follows path D3b and stimulation is increased (rather than decreased which occurs during maintenance for successful responders). If nerve activation is successful during each treatment session, then after the treatment schedule is increased (e.g., a rate of 2-3/per week is increased to every other day) and step 12' is repeated. If a positive outcome does not occur in step 13, then the patient is classified as a "non-responder". Repeating steps 12' and 13 multiple times in the case of a candidate non-responder may occur in an extended assessment interval that causes the adjustment that is made along path D3b to include, for example, switching to a different stimulation frequency, site, amplitude, treatment schedule or stimulation "dose". Alternatively, non-responders may be assessed further by stimulating both the SAFN and PTN (via percutaneous stimulation).

In an embodiment, when the assessment step 13 occurs after step 12' then negative result does not result in path D3a or D3b, but rather leads to percutaneous stimulation 10' and then assessment 13. This can occur if it is uncertain that transcutaneous stimulation is successfully modulating the nerve target such as the SAFN. It may be that assessment with transcutaneous stimulation 12' is not effective, but that subsequent assessment with percutaneous stimulation 10' may cause an assessment step 13 to yield a positive result and this can, in turn, lead to treatment with an implantable device 16 (i.e., positive responders to either transcutaneous or percutaneous stimulation are candidates for implantation). As this example illustrates, the method steps shown in FIG. 1B can be skipped and/or repeated.

In an embodiment, if percutaneous or transcutaneous stimulation of nerve is assessed as successful in steps 11 or 13, then an implantable therapy includes implantation of a device to stimulate the same nerve (e.g., SAFN or tibial nerve branch). However, a positive responder to SAFN stimulation may be implanted with a device to stimulate the tibial nerve (TN), the SAFN and TN, the SAFN and PTN, or a nerve in the leg and a spinal target (e.g., using a sacral nerve stimulator). The assessment step 11 or 13 may be repeated to compare stimulation of a single nerve target with a different nerve target, or with the combination of two nerve targets to asses the benefit of different interventions. The assessment can occur while the patient is on or off a drug regimen.

In an embodiment, a positive outcome in assessment steps 11 or 13 results in implantation of 1 or 2 stimulators in steps 14 or 16. In an example, a first stimulator is positioned near the medial malleolus provides treatment of the PTN and a second stimulator is positioned near the upper, medial calf region to stimulate the SAFN. In an alternative example, a stimulator positioned near the PTN also stimulates the SAFN. This may occur using electrode stimulators on the bottom and top side of the neurostimulator housing, respectively (if the neurostimulator is positioned between the two nerves), or by at least one stimulator on the bottom side of a neurostimulator housing (referenced to a second electrode located annularly around the perimeter of a neurostimulator) that provides a stimulation signal is strong enough to reach both SAFN and PTN targets. Additionally, if the assessment indicates that the scheduled stimulation provided by an implantable neurostimulator may be insufficient, then a stimulation protocol which uses combined internal-external stimulation can be used during treatment. For example, a single neurostimulator is implanted to treat one target such as the PTN and an external TENS neurostimulator is used to treat a second target such as the SAFN. Additionally, in an alternative embodiment, a device is implanted in a location such as near the knee to stimulate both the SAFN and the TN, while an external stimulator provides supplemental stimulation to a nerve target such as the SAFN.

External transcutaneous, percutaneous and implantable stimulation treatment can be provided in combination. For example, to decrease battery usage (and extend the battery life), or to increase the dose of peripheral stimulation above that provided by the implanted stimulation, the stimulation of an implanted device is supplemented with external or percutaneous stimulation. Combined stimulation is used, for example, if assessment in step 11 or 13 (using external stimulation) indicates that the implantable stimulation dose would be likely to be insufficient, if the stimulation of the implanted device is found to be insufficient, or to augment the rate of induction. Additionally, a patient may suffer periods of increased edema. During these times the implantable neurostimulator may be unable to sufficiently stimulate the nerve target. Percutaneous or transcutaneous stimulation provides therapy during this instance, a preferably at a different location than the implant having reduced edema.

Clinic-Based Transition to Home-Based Stimulation Therapy

Percutaneous treatment currently occurs during scheduled clinic visits, once per week for 12 weeks (termed "induction"). This is followed by treatments every 3-4 weeks (termed "maintenance") which are necessary to maintain therapy benefit. A treatment paradigm using transcutaneous treatment after percutaneous stimulation may provide an improved therapy option, which is less invasive and allows therapy to occur in the clinic, at-home, or both.

In an embodiment, a first interval 20 of FIG. 2 lasts between 3 and 12 weeks serves as induction period during which percutaneous stimulation is provided and patient reported symptoms (e.g., using quality of life or bladder diaries), behavioral measures, or other measures (e.g., objective measures calculated from sensed data) are assessed. If a patient is classified as a responder during the first interval (which serves as a first screening interval), then the first interval is followed by a second interval during which transcutaneous treatment is provided and assessed. The second interval generally is longer than the first interval or may be ongoing without a defined end date. The first interval typically uses a stronger dose (e.g., more frequent schedule) than the second interval. For example, percutaneous stimulation that occurs 3× per week is followed by TENS which occurs once per week or once every 2 weeks. Further, if during the first interval percutaneous stimulation of a first target (e.g., PTN or TN) does not meet a screening criterion, then instead of being labeled a non-responder, this can be followed by a second screening interval which entails stimulation of the SAFN, or a combination of sites, such as PTN/SAFN stimulation, or stimulation of both legs instead of one leg, increased dose, etc. Each step or iteration of the assessment protocol of the first interval may use the same or different durations. The first interval serves as assessment that occurs prior to transition to a second phase where a selected treatment is provided for maintenance treatment. In embodiments the first interval involves clinic visits for percutaneous stimulation and the second interval primarily includes at-home treatment.

The first interval 20 can serve as an induction, assessment, or screening interval. For example, patient screening can be done at the end of an induction protocol which uses more frequent stimulation than occurs in a second interval 22. In different embodiments of methods, these terms may refer to steps that provide for different outcomes or result. For example, the stimulation that occurs during an induction period is generally more frequent or has longer stimulation (e.g. 60 minutes rather than 30) than that which occurs in the second period that follows since it is used to induce benefits which are then maintained over a second interval. In embodiments, assessment may entail more than screening to obtain a positive or negative result. It may also include adjusting stimulation parameters on a schedule until benefit, or until a benefit plateau, is reached. Assessment may also include evaluating the effects of combination stimulation at more than one site related to a single site, or stimulation that is provided in combination with other treatments such as drug therapy. For example, during assessment that occurs in the first interval 20, stimulation at 2 sites on the same leg or on sites at two legs can be compared to stimulation at one site. Assessment may also include determining improved ranges for stimulation parameters. In treatment of pelvic floor disorders such as OAB, parameters in the ranges of approximately 1-30 Hz (e.g. for SAFN or TN stimulation), or over 1 kHz such as 50 kHz or 100 kHz may be assessed. High frequency carriers may be unmodulated or modulated (e.g. 50 kHz modulated at 20 Hz).

After a period of successful at-home treatment with a transcutaneous or percutaneous device, a patient may decide that an implantable device is preferable. During assessment of candidate stimulation sites for an implanted device, successful stimulation of the target nerve can be confirmation by foot twitch (e.g., PTN), subjective reports of paresthesia (e.g., SAFN), or other method such as assessment of muscle or nerve activity in sensed data. The candidate treatment area/sites may be mapped using a mapping procedure. For example, using an insulated needle with a conductive tip to assess a set of locations of the stimulator with respect to successful stimulation of SAFN and/or PTN. A partially coated stimulation needle with pin-point conductive electrode located at the tip can be used to assess stimulation at closer nerve to needle distances than using an uninsulated needle.

In embodiments, when stimulation is provided with an implantable neurostimulator then a stimulator lead can be placed posterior to the medial malleolus with a set of electrode contacts that are spaced and powered sufficiently to be positioned at a superficial location and which stimulate both the SAFN and also the PTN nerves at a deeper region. In an alternative embodiment, one lead can be situated to stimulate the PTN and another can stimulate the anterior area in the region of the medial malleolus to stimulate the anterior branch of the SAFN. Both the PTN and SAFN can be stimulated in various manners at the level of the medial malleolus. Alternatively, the PTN can be stimulated at the level of the medial malleolus and the SAFN can be stimulated higher up near the knee. Alternatively, both the TN and SAFN can be stimulated near the level of the knee such as by implanting a stimulator in the back of the leg near the knee. During therapy, an external controller 106 (see FIG. 9) is used to control the stimulation provided at one or more leads of one or more neurostimulators. After implantation, the controller 106 can be used to set the stimulation signal amplitude at, below, or above a selected level such as sensation threshold, nerve recruitment or motor threshold, reflecting that nerve activity is modulated by the stimulation signal.

Assessment & Treatment—Selecting Successful Stimulation Site(s)

Peripheral nerve stimulation, such as for the SAFN, may occur at many different locations along a patient's leg, especially at or below the knee. During assessment such as that which occurs in step 20, different sites may be assessed and selected for providing stimulation. For sensory nerves, subjective sensations of stimulation (e.g., paresthesia) can be used to select successful treatment sites from a set of candidate sites. For example, in embodiments the medial aspects of the leg may include suitable sites for stimulation starting about 3 finger widths below the knee and extending all the way down to the level of the medial malleolus or, for example, 50, 70, or 90% of that total distance. Different sites may work better for producing therapy in different individuals based upon 1) anatomical distribution of nerve pathways in an individual as assessed via imaging or mapping data 2) nerve branch density (larger branches may allow for greater nerve recruitment and likewise upstream bladder modulation) 3) patient sensitivity to stimulation (e.g. nerve recruitment threshold) 4) patient tolerance (e.g. pain/discomfort threshold, 5) differences between sensation, recruitment, and tolerance threshold 6) density of cutaneous fibers that may produce pain signals unrelated to target nerve recruitment, 7) a site's propensity for causing unwanted adjacent muscle activation, and 8) a site's range that exists between the threshold stimulation required to produce changes in symptoms and the maximum tolerable level of stimulation at that site. When the TN or its branches are assessed, motor evoked responses may be used as well. During assessment of candidate sites, at least one, but typically two or more of these factors are evaluated as a variable in the assessment and selection of one or more candidate treatment sites. When two or more candidate sites are selected on the same nerve branch of the same or different leg, then electrical data (e.g., evoked nerve activity measures) may be used to adjust stimulation parameters such as phase or delay between the at least two stimulation signals so that the combination produces an intended result (e.g., a larger response upstream such as recorded by a sensor higher in the leg or located in the bladder).

Stimulation Specificity, Spillover, Co-activation, and Multi-Nerve Activation

Studies have not yet reported the effects of co-activation of both the TN (or PTN) and SAFN. It may be the co-stimulation of the SAFN and TN (or one of its branches) causes improved bladder modulation in treating OAB when these are done at approximately the same time because they both serve to relax the patient's bladder. Alternatively, when the two are co-activated simultaneously these signals can interfere and produce a smaller effect. Not to be limited by theory, it may be that the large variation of efficacy related to PTN stimulation is due, in part, to co-activation either producing improved or worsened bladder modulation than when only one nerve is stimulated. Further, the outcome may be at least partially due to the characteristics of this co-activation. Even if simultaneous co-activation decreases efficacy, at least in some individuals, activating the two nerves at two different times may provide improved bladder modulation. For example, although the PTN projects to sacral targets through spinal connections at for example, S3/S4, the influence of stimulation of PTN/SAFN and other peripheral targets in the leg (e.g. sural nerve) may produce modulation of brain targets such as Barrington's Nucleus and, may also modulate (by relay) the medial frontal cortex, insular cortex, hypothalamus and periaqueductal gray, or structures in the rostral pons of the brainstem. These are involved in the supraspinal regulation of micturition. For example, direct or peripherally induced activation of the pontine micturition center can relax the urethral sphincter allowing for micturition to occur. Some regions of the brainstem involved with micturition send descending excitatory projections to spinally located parasympathetic neurons controlling the detrusor muscle of the bladder and inhibitory interneurons regulating Onuf's nucleus. Additionally, these central brain regions can receive ascending input from the level of the lumbosacral spinal cord, and may suggest one influence by which the SAFN stimulation may provide its benefit. Stimulating multiple peripheral nerves may cause different changes in these brain areas that are different than when only one peripheral nerve is used during treatment.

In addition to the SAFN and PTN nerve combinations additional targets used alone or in combination include the medial plantar nerve, lateral plantar nerve, peroneal nerve, sacral nerve stimulation, lumbar nerve stimulation (especially L2, L3, L4), pudendal nerve, dorsal genital nerve, and the vagus nerve. In embodiments, these nerve targets are used to treat disorders related to pelvic floor disorders, micturition disorders, disorders of the autonomic nervous system, or other disorders.

The relay of nerve activation signals from peripheral to central structures can alter the activity of the brain in time-locked manner. It may be that stimulation of the PTN/SAFN can be detected by somatosensory evoked potential or other evoked potential which can provide an objective measure of peripheral nerve recruitment. As is well known, analysis of relevant data related to the brain, heart, or peripheral nerve activity can be assessed in the time or frequency domain via Fourier or other signal processing method (and may use templates or algorithms to identify waveforms such as heartbeats and intervals between peaks, to assess either baseline or changes due to stimulation). For example, microneurography can be used to assess a difference in nerve activity that occurs with and without associated stimulation. Nerve stimulation can be confirmed by looking at the difference before and after stimulation in a time-locked manner or alternatively baseline compared to treatment interval manner.

In embodiments, the parameters for stimulating the two different nerves are independently set for an implanted device stimulation 14. A neurostimulator is designed to stimulate with a paddle electrode positioned between the SAFN and PTN, and to stimulate an area superficial to the paddle using a SAFN protocol and an area deep to the paddle with a PTN protocol. Alternatively, if the electrode is disposed on an annular configuration, as can occur with a BION type device and co-activation of the SAFN is not desired, then a non-insulating shield element (e.g. a silicone or other non-conductive sheet) can be surgically positioned superficial to the annular electrodes so that stimulation energy does not unintentionally stimulate the more superficial SAFN branches during stimulation of the PTN.

There is much still to be understood about bladder reflex pathways and the invention is not meant to be limited by current understanding and theory. On theory is that pathological parasympathetic or sympathetic activity can lead to incorrect operation of the micturition system both in terms of function/operation and also with respect to leading to unwanted symptoms. Peripheral stimulation may be used to reset/restore the system. The stimulation adjusts the system to again operate more normally, at least in an acute manner. Stimulation can also disrupt pathological activity of the system. In an embodiment, the stimulation is provided to modulate at least one brain or spinal cord autonomic feedback loop associated with bladder activity and uses data relating to urinary or other voiding symptoms of a patient as a feedback signal. In an embodiment, at least one stimulation parameter or stimulation site is selected which increases the parasympathetic activation and/or decreases sympathetic activation. In another embodiment, at least one stimulation parameter or stimulation site is selected which decreases the parasympathetic activation and/or increases sympathetic activation. In another embodiment, at least two stimulation parameters and stimulation sites are selected wherein the first site of stimulation causes the parasympathetic system to experience relative activation or deactivation (compared to that which occurs in the absence of stimulation). The second stimulation site causes sympathetic deactivation or activation. Accordingly, the two sites serve to reinforce a desired net change.

Multi-nerve stimulation at two or more sites (or stimulating a single nerve at two or more sites) in the same or in both legs, will produce larger therapeutic results than single nerve stimulation, at least in some individuals. In embodiments the stimulation signals at two or more stimulators are adjusted to occur at the same time (with or without relative offset between the two signals), in an alternating manner, at different times, at different times separated by selected intervals, and in other manners. When both legs are stimulated using at least one neurostimulator, then the stimulation can be coordinated by a single patient controller device 106 to control stimulation provided by at least one implantable, external, or percutaneous stimulator.

Hypertension, Obesity and Other Disorders, Dysfunctions, or Unwanted Health States In embodiments, peripheral nerve stimulation provides for modulation of blood pressure during or after stimulation. Stimulation of at least one of the SAFN, TN, PTN, median, and/or other peripheral nerves is used to modulate cardiovascular health such as causing blood pressure changes. The assessment (e.g., patient screening) and treatment methods disclosed earlier in this specification which focused upon OAB treatment as an example are adopted for treatment of hyper-/hypo-tension or obesity. Candidate nerve targets for treatment of abnormal blood pressure include, for example, the median nerve, and more specifically targets corresponding to points P5 and P6 (used in acupuncture and electroacupuncture). For example, during treatment for hypertension using the median nerve, at least one stimulation frequency within the 2-15 Hz range, or other ranges, is used. The stimulation signal is realized as a monopolar or bipolar pulse train or as an envelope that modulates a high frequency pulse train, such as between 10 kHz to 50 kHz or 100 kHz (or higher). Use of high-frequency carrier waveforms can provide advantages during transcutaneous and percutaneous stimulation such as decreased risk of pain, greater transmission of energy through tissue, and unique heat signatures in tissue that receives the stimulation signals for improved patient comfort and modulation of a nerve target.

When used to treat a disorder such as abnormal blood pressure the assessment includes measurement of blood pressure (e.g. systolic, diastolic, or both) using a site on the hand, leg, arm, ear, or other body part. Arm-based cuff-measurement of blood pressure is a preferred embodiment. Preferably, the location used at the start and end of the assessment period to sense a pressure measurement should be approximately the same same. Additional measures that reflect sympathetic or parasympathetic activation are also used to assess the effects of stimulation either during or after the stimulation. Measured data can be used to guide the adjustment of stimulation parameters. This can occur control of a in a closed-loop (or control law) algorithm of a control module 72 (see FIG. 7).

In an embodiment, stimulation using transcutaneous, percutaneous, or implantable stimulation of a peripheral target such as the SAFN or median nerve allows assessment and screening of patients who are candidates for renal nerve ablation using RF, alcohol ablation, or other means. Without being limited by theory, response to peripheral electrical nerve stimulation may indicate the patient would be a good candidate for renal nerve ablation and can be used to screen candidate patients prior to the procedure. In an alternative embodiment, a responder to peripheral electrical stimulation may be used to determine patients who may avoid renal nerve ablation since this alternative therapy is effective. Additionally, peripheral nerve stimulation may be used in combination with ablative therapies to increase benefit after ablation. since renal nerve ablation is a recently developed technology and it is not currently known whether ablation may cause certain individuals to suffer from hypotension or other disorder or cause other dysregulation of cardiovascular health and/or balance years after the procedure. Accordingly, peripheral nerve stimulation can be used to modulate blood pressure in renal nerve ablation patients who experience difficulties months or years after treatment due to a loss of renal nerve activity.

In addition to hypertension, systems and methods disclosed herein can be used to provide desired changes and symptom relief in a wide number of conditions such as obesity, addiction, and other disorders, dysfunctions, or unwanted health states.

At-Home Percutaneous Treatment

Figure 3A:
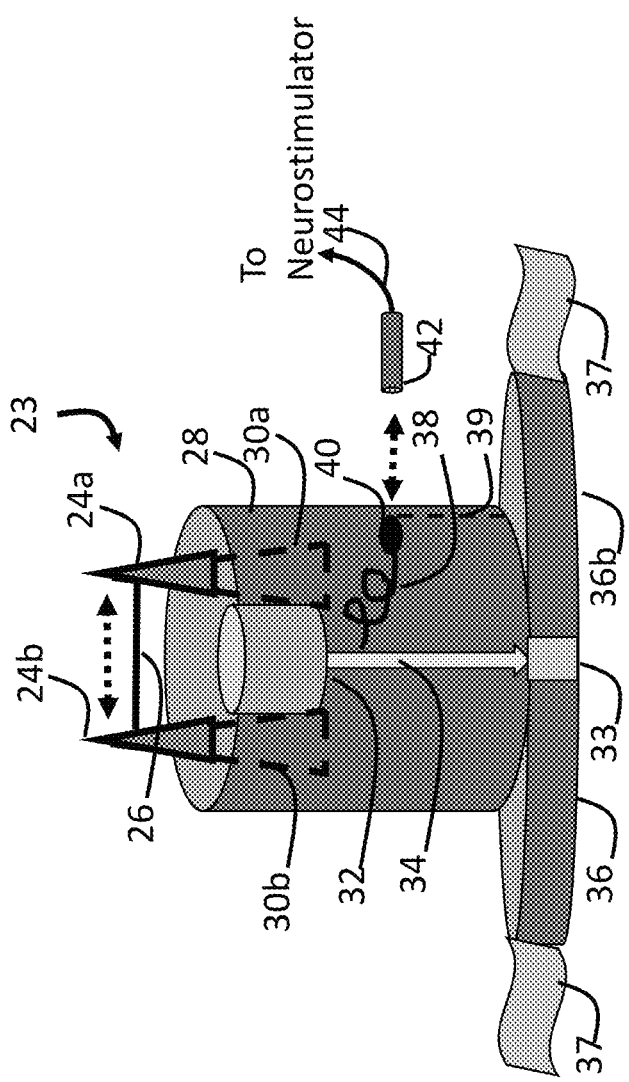

FIG. 3A shows an embodiment of a percutaneous accessory 23 device for facilitating injecting and stimulating with percutaneous stimulation. The accessory 23 includes a housing 28 with a biasing means such as a spring 32 configured to press needle 34 through guide 33, a base portion 36 configured to be applied to a patient's skin via adhesive a base portion bottom surface 36b, and/or securing means such as a strap 37. In the example, the strap attaches to two areas of the base portion. Velcro regions can be used to secure the accessory 23 to the patient's limb. Additionally, the guide 33 can have various forms such as including one or more disks each having a circular gap or rods having loops through which the needle 34 passes. The spring 32 typically resides in an undeployed position prior to use. It may be retained in compressed position by at least one latching or restraining member. For example, a pair of retaining arms 30a, 30b normally inhibit movement and are operated to an "open" position which permit movement of the needle when a user pinches tabs 24a, 24b together. If tabs 24a, 24b are separated by biasing member 26, then this is deformed or broken when the needle is deployed. The housing 28 has a port 40 connected by conduit 38 (internal to the housing) to the needle 34 to communicate stimulation signals from a connector 42 which plugs into port 40 and provides signals from a neurostimulation device using external conduit 44. Base portion 36 and other regions of the housing may be transparent to enable viewing of the needle and skin target location.

In embodiments, the housing 28, base portion 36 and other components of the accessory 23 are of suitably rigid and non-conductive material such as plastic, and may also be flexible or cushioning material (e.g., foam, rubber, silicone-materials, polymers, neoprene, polyethylene naphthalate, co-polymer plastics). Gels serve as adhesive and/or conductive mediums on surfaces that contact the user. Topical antibiotics can also be used to deter infection. Typically, the housing 28 and base 36 are substantially nonconductive except for the components that route stimulation signals. Although base portion 36 is shown relatively flat relative to the housing 28, the accessory 23 can be different shapes. In the embodiment shown, a second internal conduit 39 routes signals from the port 40 to a conductive region on the bottom of the base section 36b to complete an electrical circuit with the needle 34 (e.g., serve as anode or cathode). Alternatively, the circuit includes a TENS pad which is affixed to the patient's skin and connected to the neurostimulator. The conduit 38 may be multi-stranded and the needle 34 has both non-conductive regions and electrical routing to serve as a bipolar electrode.

FIG. 3B shows the needle percutaneous accessory 23 in a "deployed" position. The spring 32 is deployed and the tops of tabs 24a, 24b are closer than in FIG. 3A, having been "pinched" together by a user. In an embodiment, a non-conductive coating (e.g., acrylic, polyurethane, silicone, plastic, etc.) resides on the surface of the needle 34 and only a conductive tip 41 region provides the stimulation signal to a nerve target. Not to be limited by theory, a needle with a non-conductive region along a large proportion of its surface and a conductive tip surface may provide advantages. For example, a needle with a conductive surface limited to its tip isolates the stimulation signal from the superficial dermal layers and nerves that could typically cause pain during stimulation at a location such as the upper calf. Additionally, this configuration can allow selective stimulation such as of different nerves in the leg. In embodiments, the accessory 23 is configured to be injected 0.5 cm to 1.0 cm, or 1.0 cm to 2.0 cm, to stimulate the SAFN or PTN, respectively. Longer injection depths may also be used.

In embodiments, accessory 23 is designed as single-use and disposable. Other designs allow repeated-use with needles that are replaceable and disposable. The accessory 23 is provided with a manual means of re-setting the spring mechanism and restoring the biasing member 26 similar to lancet devices designed to draw blood in diabetics and allowing "spring reset" and disposable needles.

When a needle is used to provide treatment and percutaneously stimulate the SAFN or PTN (or other nerve or nerve branch) it may be formed to provide at least one conductive surface region 41 along a non-conductive shaft surface. For example, a non-conductive coating can be used to create at least one non-conductive region on the shaft surface of the needle generally near the needle tip. Without being limited by theory, it may be found that using a needle which has a conductive tip surface and is non-conductive along the remainder of the length of its surface which is inserted into a patient can increase the selectively of nerve stimulation and this may be thought to provide improved target selectivity. It may be that stimulating the SAFN or PTN independently is more efficacious than stimulating both concurrently, or it may be that different stimulation parameters may be desired for stimulation of these two nerves. In addition to a conductive tip surface, other portions of the needle may surface can also be provided which are not coated by the insulative coating to create 2 or more conductive annular rings. These rings may be spaced in relation to the intended nerve targets. In an embodiment each of these rings can be connected to insulated micro-lead wires that run the length of the needle to independently communicate signals between the rings and stimulus generation circuitry.

Figure 4B:
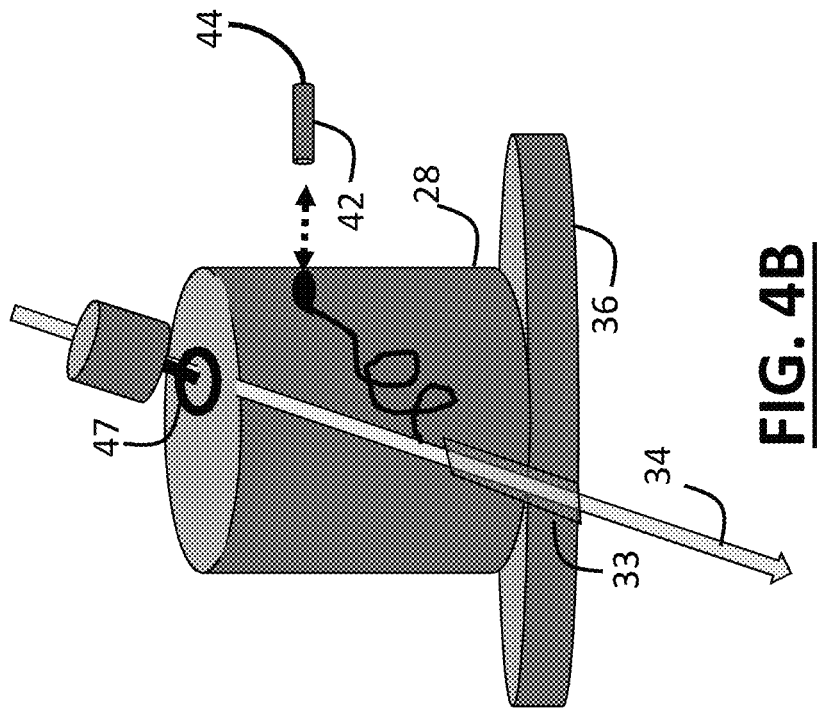
FIGS. 4A and 4B show an alternative embodiment percutaneous stimulation accessory in an undeployed and deployed state, respectively.
Figure 4A:
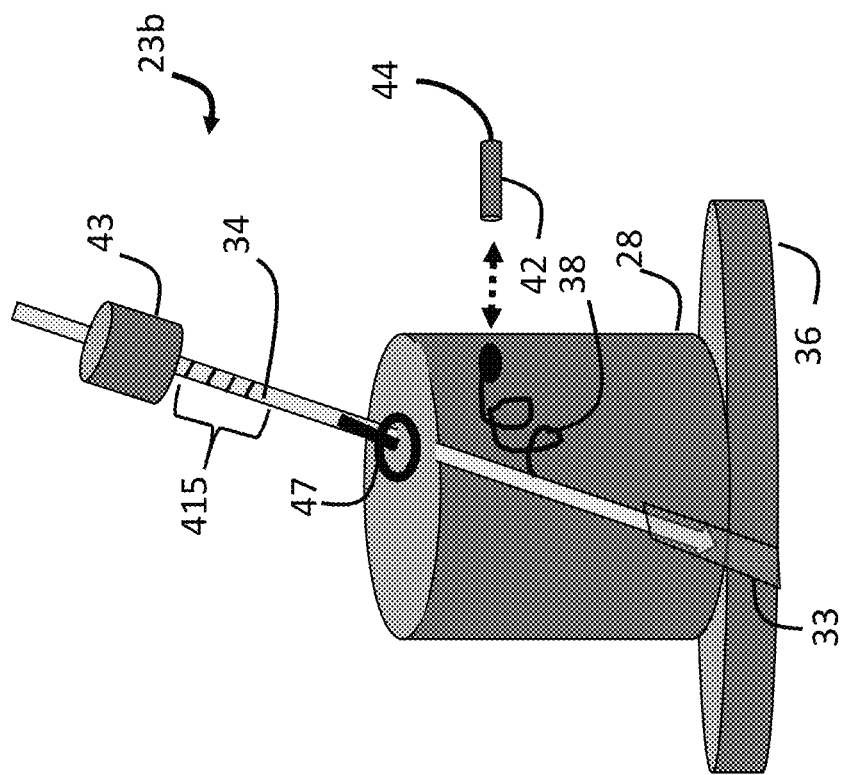

FIG. 4A shows an alternative embodiment of a percutaneous accessory 23b where the needle 34 stimulator punctures the skin at an angle defined by the combination of a guide 33 and opening 47. The angle may be between 0 and 90 degrees and may be set depending upon the nerve target to be stimulated. In embodiments, the angle is limited to a smaller range such as 30-60 degrees. During operation, the needle 34 is manually slid through an opening 47 in the accessory housing 28, by a user so that it moves through the base section 36 and into the patient. A blocker or stop block 43 which has a larger cross-sectional area than opening 47 restricts the depth of needle 34 injection to a predetermined range of depth (e.g., <3 cm). The position of the block 43 can be adjusted by a user so that it aligns with at least one of a set of notches 415 on the needle shaft 34. Alternatively, different models of the accessory may have pre-set positions for the block 43. The position of the block may be determined in a clinic by a doctor who assesses the range of depth typically required to provide percutaneous stimulation of a patient. Accordingly, accessory 23b provides a medical solution by which the angle and depth are constrained within ranges that reflect what is used during treatment by a trained medical practitioner.

FIG. 4B shows an embodiment of the percutaneous accessory 23b in a deployed position. The housing 28 and base member 36 are substantially transparent or translucent and formed using a plastic, acrylic, or glass to enable alignment of guide 33 of the base section 36 with an intended injection site. The target site can be marked by a "dot" tattoo at a site previously determined to successfully provide stimulation of a target nerve. The accessory 23b can also be realized without the conduit 38 or port 40 in the housing 28 and serves only to inject the needle. After injection, it is removed, and the needle 34 is connected to a neurostimulator.

Figure 4D:
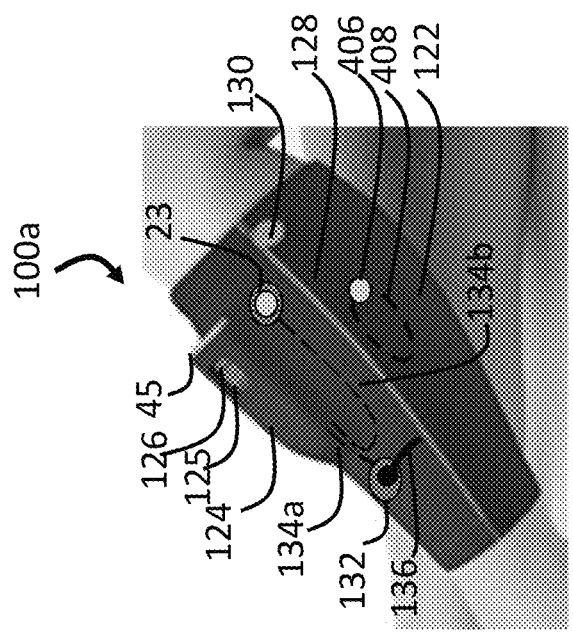
FIG. 4D shows a wearable neurostimulator having both a percutaneous stimulation accessory and biased TENS pad for improved nerve recruitment.
Figure 4C:
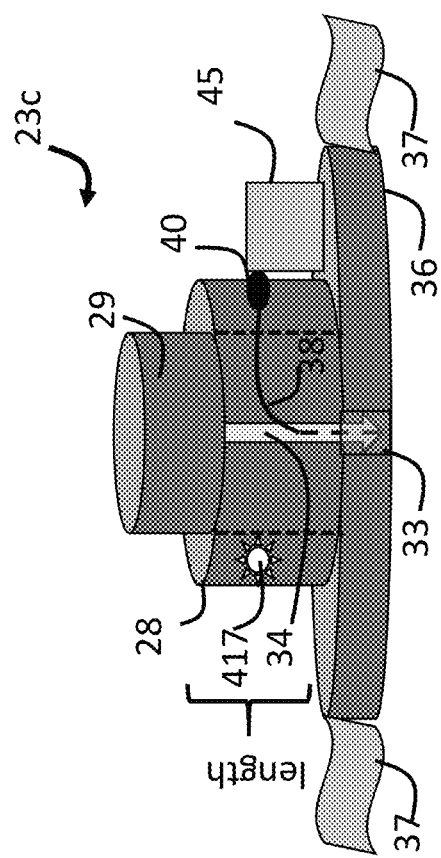
FIG. 4C shows an alternative embodiment percutaneous stimulation accessory in an un-deployed state.

FIG. 4C shows an embodiment of the percutaneous accessory 23c designed with a push-button control 29 on the top of housing 28 that deploys the needle 34 when pressed. The housing 28 length corresponds to the intended injection depth. Accessory models can be selected to have different lengths according to different target sites or patient anatomies. Although the housing is approximately rigid (e.g., made of a plastic or hard rubber), in an embodiment the button control 29 is manufactured to be deformable with a collapsible matrix within its volume. Accordingly, when pressed by a user, the top of the button control 29 causes selected portions of a matrix to collapse and pushes the button cover and by extension the needle downward so it is positioned at a desired depth. Alternatively, the push button is configured to be rigid and to be slide down into a cylinder formed within the housing 28 (defined by dotted lines) so that it displaces the needle and causes injection when it is driven down into the housing 28 of the accessory 23c. In other embodiments, the button control 29 is engaged by a latching ratchet mechanism within the housing that engages with the button control as its moves downward and provides iterative securing of the button as the needle is injected. The button control 29 can be either biased or un-biased. For example, a spring can bias the button control 29 towards its un-pushed state to offer resistance, and latching control to retain the button (and needle) in the deployed state. Alternatively, the button control 29 is configured with a securing element that allows the needle to be slid down through the housing 28 and towards the skin with ratchet, latching, or locking mechanisms to maintain desired depth position of the needle. In the shown embodiment, the accessory 23c has a neurostimulator 45 connected to port 40 to deliver a stimulation signal through the needle 34. The neurostimulator 45 can also provide a signal to a conductive region on the bottom 36b of the base member 36 or to a conduit that leads to a TENS pad (not shown). The percutaneous accessories shown in FIGS. 4A-4C each use only one needle. The mechanical and electrical designs can be adjusted so two needles of same or different lengths are deployed. Battery power/circuitry can be included to provide the accessory 23c with more features (e.g., timers, impedance testing circuitry and indicators, etc.)

As FIG. 4C illustrates, in an embodiment a nerve treatment system for delivering electrical signals to a target nerve includes a housing 28 having a base member 36 adapted to be mounted contiguous an external skin layer of a patient and a displaceable stimulator needle 34 that is positioned within the housing 28 to provide percutaneous displacement of the displaceable stimulator to a predetermined depth beneath the external skin layer of the patient. A connector port 40 connects to a conduit 44 to electrically connect the displaceable needle stimulator 34 to a signal generator of a neurostimulator 45 or directly to the neurostimulator. A percutaneous stimulator displacement mechanism for displacing said stimulator to said predetermined depth beneath the external skin layer of the patient to a location adjacent to or contiguous with a target nerve to be treated is provided by various means. For example, button 29 that travels along predetermined range causes the maximum depth of injection to be limited. The base member 36 has an electrically conductive region to allow the signal to travel between it and the needle stimulator. The neurostimulator 45 is electrically coupled to an electrical generator that it operates as part of its stimulation module and to the needle stimulator through a conduit configured for transmitting electrical stimulation signals from the electrical generator to said needle stimulator. The housing includes at least one stimulator guide passage 33 for receiving said displaceable stimulator 34. The housing displaceable stimulator guide passage is realized in an alignment (e.g. linear) with a base member guide passage for providing a guide path for said displaceable stimulator.

In an embodiment, the housing displaceable stimulator guide passage and said base member guide passage 33 are substantially perpendicular to a planar portion of a top surface of the housing 28. Alternatively, the housing stimulator guide passage and base member guide passage 33 form an acute angle with respect to base member 36.

In an embodiment, the housing 28 includes an electrical housing port 40 formed in a sidewall of said housing for receipt of the connector 42 for example to conduit 44. For example, the conduit 44 is electrically connected on opposing ends thereof to said port 40 and said neurostimulator 45. The port is also attached to a first electrically internal conductive conduit 38 connected on opposing ends respectively to said displaceable stimulator 34 and said housing port 40. As shown in FIG. 3A, a second electrically internal conductive conduit 39 is connected on respective opposing ends to said housing port 40 and an electrically conductive region of said base member 36*b*.

As shown in FIG. 3A, in an embodiment, percutaneous stimulator displacement accessory includes a spring biased member 32 coupled to said displaceable stimulator 34 for maintaining said displaceable stimulator within the confines of a housing 28 in an un-deployed state and release of the displaceable stimulator to be displaced percutaneously in a deployed state (see FIG. 3B). A displaceable locking member is realized, for example, by retaining arms 30*a* and 39*b* for bearing against said spring biased member to maintain said displaceable stimulator in an un-deployed state and releasing said displaceable stimulator in a deployed state. Alternatively, the displaceable locking member can include at least one displaceable tab member mounted to the housing 28 which is fixed to said spring biased member in said un-deployed state and released from said displaceable stimulator in said deployed state.

Alternatively, as is shown in FIG. 4A, an accessory is shown having a percutaneous displaceable stimulator is slideably displaceable within said housing 28 displaceable along a guide passage formed from an opening 47 and said base member guide passage 33. The including a stop member 43 that is fixed to said percutaneous stimulator at a predetermined location, or at an adjustable lcation, to permit said displaceable stimulator to be positioned at said predetermined depth beneath the external skin layer of the patient. In this shown embodiment, the stop member is a block member 43 which contacts an upper surface of said housing 28 when the displaceable stimulator 34 has reached said predetermined depth beneath the external skin layer of the patient.

FIG. 4D shows an embodiment of a wearable neurostimulator device 100*a* having both a percutaneous stimulation accessory 23 and biased TENS pad 132, that is pressed against the patient's skin so that both pressure and electrical stimulation are provided. This allows improved nerve recruitment by decreasing the amount of tissue or distance between the pad 132 and a target nerve. Although both percutaneous and transcutaneous stimulators are shown, the device may be realized to only use TENS pads and with multiple pairs of pads and to provide both stimulation and sensing under control of the neurostimulator. In an embodiment, a wearable garment 122 such as leg wrap of a suitable material such as neoprene is formed to be worn by a user after being secured such as by at least one fastener (e.g. zipper 128 or clasp 130). The wearable garment 122 contains a pocket 124 within which resides a neurostimulator 45 having a display 126 that can be seen through an opening 125 formed in a wall of the wearable garment 122. The wearable 122 is configured with at least a first electrical conduit 134*a* that routes a stimulation signal to at least a first TENS pad 132 that is configured to be attached to wearable garment 122 and neurostimulator 45 so that it provides stimulation to the patient's skin. A second conduit 134*b* communicates stimulation signals between the neurostimulator 45 and a percutaneous accessory 23 that can be inserted into the wearable garment 122 and connected to the conduit 134*a* to allow a needle stimulator to be used to provide percutaneous stimulation. The wearable stimulation device 100*a* is configured with at least one biasing member 136. In an embodiment the biasing member is a plastic or metallic arm that is configured to press or bias the TENS pad towards the skin of the user and closer to the target nerve. For example, a spring can be attached to the arm and the garment and configured to pull the arm towards garment. In an embodiment the metallic arm is provided as part of the inner surface of a separate band that wraps around the leg. The biasing member can provide pressure-TENS where the stimulation pad is pressed towards the target nerve with a pressure that is sufficient to increase the chance of successful nerve recruitment. More than one arm can be provided to cause one or more stimulation pads to be biased at one or more locations towards the subject's skin and towards the target nerve and to retain the stimulation pad in an intended position. In an embodiment the device 100*a* incorporates a pump 406 and bladder 408 system which allows for adjustment of pressure at one or more locations. The bladder is disposed, for example, within the wearable garment 122 or between the garment and the user's skin, or between the garment and electrode array. While the bladder is typically disposed near at least one stimulation pad to bias the pad towards a target nerve the pump 406 and bladder 408 system is shown in a location selected to avoid cluttering of the figure. The pump design allows for at least one of manual or powered pumping.

In an embodiment, the device 100*a* uses its stimulation/sensing module 76 to provide percutaneous sensing using a percutaneous needle and at least one stimulation pad, and stimulation is provided using two or more transcutaneous stimulation pads 132, or a single stimulation pad with two conductive stimulation areas. Further, when sensing is provided by stimulation/sensing module 76 then a first pair of stimulation pads 132 provide nerve stimulation while a second pair of transcutaneous pads 132 provide sensing.

FIG. 4E shows an embodiment of a wearable neurostimulator realized within a wearable garment 122 for attachment to a user such as an elastomeric neoprene band which is configured to receive a TENS stimulation pad 140. The pad 140 fits within a stimulation region 141 in the garment. The stimulation region 141 is realized simply as an opening in the fabric, or includes a plastic frame (shown as dashed line) that is connected to the fabric and which may serve as a ferrule. The stimulation pad 140 is biased towards the skin of the subject by a bottom side of biasing mechanism 138 which is realized as a spring in the illustrated embodiment. The top side of the spring is secured against a rigid cover member 146. In an embodiment the rigid member 146 and biasing mechanism 138 can be snapped onto the garment 122 material or onto a plastic frame of the stimulation region 141. In an alternative embodiment the rigid cover member is attached to the garment (or frame of the stimulation region) using a hinge on one edge and a locking mechanism on the other edge so that the rigid cover member 146 may be rotated and locked into place.

FIG. 4F shows an alternative embodiment of a wearable neurostimulator realized using a garment 122 for attachment to a user such as an elastomeric neoprene band which is configured to receive a TENS stimulation pad 140. The stimulation pad 140 is biased towards the skin of the subject by biasing system comprising a pressure adjustment controller 144 which works in conjunction with a rigid cover member 148 having a grooved or threaded opening 143 within the cover member, which allows the controller 144 to be operated to adjust the pressure that is exerted onto the stimulation pad. In the embodiment shown, the controller 144 is shown with a threaded cylinder which is received by a threaded portion 143 of the rigid member 148 so that it may be rotated to adjust pressure. However, in alternative embodiments, the controller is configured so that it may be ratcheted or otherwise adjusted to bias the stimulation pad 140. A pressure sensor 142 is shown disposed to measure the pressure exerted on the stimulation pad by the controller and this may be electrically connected to the sensing module of a neurostimulator by a conduit (not shown). In an embodiment the rigid member 146 and biasing mechanism 138 or 144 can be snapped onto the garment 122 material. In an alternative embodiment the rigid member or cover is attached to the device using a hinge 149 on one edge.

FIG. 4G shows a top-view schematic of alternative embodiment of a wearable neurostimulator realized using a garment for attachment to a user such as an elastomeric neoprene band. The garment has two lateral garment portions 122a, 122b, and a central portion 122c which is configured to receive two TENS stimulation pads. A first stimulation region 141 which is on the top figure houses a tens stimulation pad 140 that is biased towards the skin of the subject by biasing system comprising a biasing means 138 (e.g. a spring) that is attached to a rigid cover member 148 which is rotatably connected to the band 122c by way of hinge 149. The stimulation pad 140 is electrically connected to a neurostimulator 45, by conduit 66. The second stimulation region 141 contains a pressure adjustment controller 144 which works in conjunction with a rigid cover member 148 having a grooved or threaded opening disclosed in the description of FIG. 4F.

FIGS. 5A, 5B, and 5C show embodiments of TENS electrodes used to provide stimulation of nerve targets such as those in a limb (e.g. a leg for SAFN stimulation). Although two conductive portions are shown in each stimulator design, other designs with 3 or more conductive elements are also within the scope of the invention. The bottom side of the electrode pad(s) contact the user's skin and the side going into the page (i.e. top side) is connected to a neurostimulator 45 having a stimulus generator which provides electrical conduits 66a, 66b to at least two conductive surfaces 46a, 46b of the pads which form an electrical circuit (e.g. serve as anode and cathode). As is known to those skilled in the art the conduits 66a,66b may have a large number of mechanisms for being connected to the surfaces 46a, 46b, such using a terminal connection 55, such as pair of male/female conductive snaps 55. For example, a back-side of the conductive surface 46a may have a female snap that receives a male snap of the conduit 66a to form a terminal connection 55. In an embodiment, a first conductive element 46a (e.g. a conductive surface coated with conductive hydrogel) is formed within or upon a larger non-conductive surface 48a of the pad, and a second conductive element 46b is provided as a return electrode. The non-conductive surfaces 48a, 48b have adhesive coatings to assist with securing the pads to the user. While both non-conductive and conductive adhesives (e.g. gels) can be shaped so the conductive and adhesive portion only overlaps the conductive element, the conductive gel may extend further than the perimeter of the conductive elements 46a. In an embodiment, the conductive elements 46a, 46b are aligned perpendicularly to the dominant orientation of the nerve target. Alternatively, these are oriented with up to 90 degrees offset to be approximately parallel to the nerve pathways.

In embodiments, the width of at least one conductive element is approximately 4, 8, 12, or 16 mm. Further the TENS stimulators are configured so that the spacing between the closest edges of the conductive portions are set at 4, 8, 12 or 16 mm, although larger distances such as 25-75 mm are also possible. For example, to increase the ability of the field to recruit a nerve distances of 100 or 150 mm may be used. Distances may be adjusted contingently upon the successful recruitment the target nerve.

FIG. 5B shows an electrode array 50 with two conductive elements 52 and 54 fashioned within a non-conductive substrate 51. In this embodiment the top electrode is narrower than the bottom electrode and produces a relatively higher current density in the proximal stimulation location. In an embodiment, the second conductive element 54 is set to be between approximately 1× to 10× the width of the first conductive element 52. Without being limited by theory, this configuration may assist nerve modulation by focusing the field to a smaller area of the nerve and/or evoking a more coherent response from the stimulated fibers. This embodiment also shows a deformed surface 58 which is realized as a central ridge aligned in the proximal to distal direction in the figure. When stimulating a nerve in the leg, deforming the stimulation pad using a raised surface may permit this area to push into the users skin and be positioned closer to the target nerve. Rather than a single deformation, multiple portions of the stimulation pad may be raised to push into the skin further than would occur with a flat surface. For example, the width of a deformed ridge may be 1 mm and the length could be 3 cm. The size and shape of one or more raised surfaces may serve to position the surface closer to the nerve using pressure and is not designed to puncture the skin, as occurs with one or more needles that may be used to provide stimulation.

FIG. 5C shows a first conductive element 56 formed on a non-conductive substrate 51 and having at least one non-uniform edge (e.g., ridged or undulating). In some individuals, this may allow higher stimulation to be provided without producing discomfort in a patient. Additionally, when the conductive element is coated with a conductive gel, the gel may be both conductive and be coated with lidocaine or other analgesic agent to deter the risk of pain during stimulation. Use of an analgesic gel may also be helpful in enabling a patient to detect nerve recruitment paresthesia at locations that are not directly under the conductive elements. In an embodiment, the strength of the analgesic gel containing lidocaine may be from approximately 3% to 25%, with an adhesive (and conductive) material containing 7% lidocaine for a 10 cm×5 cm conductive element (or TENS stimulation patch). The concentration can depend upon the total number of stimulation pads, their size, and the distance between two or more conductive elements.

FIG. 5D shows an example of an electrode array that has biasing members that serve to bias the electrode positions closer to the target nerve. It is illustrative and only one of the example biasing members may be incorporated into the design in actual practice. In the example, an electrode array 50 is formed using a non-conductive and flexible substrate 51. The array 50 is designed to be used within a portable device 100a such as that shown in FIG. 4D. For example, the array 50 is snapped onto the inside of a garment 122 and is connected to conduits 134b by terminal connectors 55a,55b, 55c. The connectors in turn transmit a stimulation signal to stimulation pads 140a, 140b, and 140c by way of conductive channels. For example, the stimulation signal travels from terminal connector 55a through conduit 38a to the top side of a support pad 402a which connects on its bottom surface to a stimulation pad 140a. A conductive connector 400a on the stimulation pad engages with the connector of the support pad 402a. A biasing member 138a, implemented in this example as a spring, is connected the support pad 402 and the array substrate 51 and serves to bias the stimulation pad 140a against the user's skin. Additionally, there is an alternative biasing member 404 realized as a plastic spacer or shaped displacement barrier that causes the support pads 402b, 402c to be positioned closer to the skin when external pressure is provided to the array 50 by way of a garment 122 that is wrapped around the user's leg. Additionally, biasing members 138b and 138c can provide additional displacement of the stimulation pads 140b and 140c towards the target nerve.

The biasing members 138a, 138b, 138c, and 404 are shown as mechanical member that are not adjustable and which do not change over time. In embodiments, these may be realized as adjustable cylinders, or pneumatic members, that may be adjusted by air or hydraulic pressure that is provided by one or more pumps. When one or more pumps are powered and under control of a neurostimulator 45 or user device 106, then the amount of pressure applied to one or more of the stimulation pads may be programmable and adjustable. Additionally, if the adjustable biasing means are independently operable then the pressure can change over time to avoid pressure from being applied to the same location on a user's leg for the entire treatment. It is an advantage to the invention to provide pressure TENS in a controllable, adjustable, programmable, and time varying manner to improve patient comfort related to the provision of therapy. The one or more pumps can also be realized within the garment and can enable a user to increase pressure by operating a pump to allow one or more cavities or "bladders" in the garment to fill or deflate. For example, the device 100 garment may include at least one bladder shaped to secure the stimulation pads against a user's skin at one or more locations. The bladder may include a plurality of chambers with a valve disposed therebetween to selectively inflate the chambers. The inflatable bladder communicates with a lightweight pump (which may be disposed thereon) which may be manual or powered. In an embodiment the system incorporate a pump 406 and bladder 408 system such as that disclosed in U.S. Pat. No. 5,113,599A, entitled "Athletic shoe having inflatable bladder" or U.S. Pat. No. 9,060,564B2 entitled "Adjustable multi-bladder system for an article of footwear", both incorporated by reference herein.

As shown in FIG. 5E, in an embodiment the device includes biasing member for positioning stimulation closer to a target nerve that is realized as at least one exoskeleton 410 structure. For example, a structure (e.g. plastic or rubber) that is deployed at least partially along the surface of the wearable material 122. Alternatively, the biasing member may be an endoskeleton 412 structure that serves to deform one or more portions a wearable garment 122, or bias a stimulation pad, and which is deployed within layers of the garment or within the non-conductive substrate 51 used in an electrode array. The endoskeleton 412 may be formed within an array 51 or within the wearable material 122. An example of an endoskeleton is at least one plastic structure that is sewn into or otherwise resides between two layers of garment 122 material. The exoskeleton and endoskeleton structures can serve to deform stimulation areas when secured to a user or otherwise distribute pressure that is applied at selected locations on user such as at one or more positions that correspond to where stimulation is provided.

Providing and adjusting one or more amounts, locations, and patterns of pressure can improve transcutaneous stimulation and overcomes problems that may occur when providing nerve stimulation. These may include factors that contribute to greater distances between at least one region of the stimulation pad and the target nerve such as anatomical variations of tissue, fat, fluid and anatomy found in different patients. These factors may also lead to increases in threshold level of stimulation amplitude required to allow for nerve recruitment, a decrease in the maximum energy that can be provided to a nerve which also does not cause cutaneous pain to a subject, a greater dispersion of the field prior to reaching the nerve, and other factors that can decrease or prevent therapeutic benefit. For example, providing pressure to at least one region of a stimulation pad has been found by the inventors to enable increased nerve recruitment which is absent (or less) when pressure is not provided. Additionally, edema or normal fluid accumulation of a patient may deter successful nerve stimulation, especially for targets in the leg or limbs. Use of pressure in combination with a stimulator during TENS, eTENS, eTMS, (or with induction using RF or magnetic schemes) can improve therapy by positioning a stimulator closer to a target nerve. The redistribution of tissue through use of pressure may also be used to position one or more sensors closer to a target nerve region to facilitate recording of sensed data related to nerve activity such as evoked nerve activity that can be used to confirm successful recruitment of a target nerve.

As shown in FIG. 5F, in an embodiment at least one stimulation pad 132 is provided with a bottom surface having at least one raised region 414a that resides on a flat bottom surface 416 of the stimulation pad. Both the flat surface 416 and raised region 414a are typically electrically conductive and comprised of the same material, however only the raised region may be conductive. When the stimulation pad is used to stimulate the saphenous nerve, then the stimulation pad is preferentially oriented within an electrode array or device 100a so that at least one raised region approximately aligns with the axis of the limb. When a second raised portion 414b is also shown which is aligned with the first. In an embodiment, the first and second raised portions reside on a conductive flat bottom surface 416 and are each raised the same distance from the surface about 2-4 mm offset from the bottom surface 416. The raised region can be any shape and the shape may be adjusted based upon characteristics such as the anatomy, tissue, amount of fluid/edema between the skin and a target nerve, or other characteristics of the region on the user where one or more pads 132 are attached. The pad 132 may also be used to sense nerve activity. Since the bottom surface of the stimulation pad 132 is flat, when pressure is applied to the stimulation pad, at least a portion of the raised region should be biased towards the target nerve and may serve to physically displace and deform any intervening fluid or tissue so that the distance between at least a portion of the stimulator/sensor is decreased with respect to a target nerve. The one or more raised portions are normally configured with size and shape characteristics that deform, rather than penetrate, tissue.

In an embodiment, two conductive pads are attached to a spring or clamp mechanism and are positioned in opposition on the medial and lateral aspects of a leg so that the pressure moves the pads towards each other and reduces the distance between the pads. The pads are used for stimulation or sensing from a target nerve in a limb. For example, the two pads can be positioned on the lateral and medial aspects of the leg and biased inward to sense from or to stimulate SAFN or PTN targets.

The systems of the current invention may be realized with external system components, internal components, or a mixture of the two. FIG. 6A shows an enhanced TENS (eTENS) passive implantable component (IPC) comprising a non-conductive substrate 60 (e.g. silicone) and a conductive region 62 (e.g., a conductive metallic alloy realized as a conductive strip or mesh). Systems and methods for eTENS have been previously described by the inventors (e.g., WO2015079391, Systems and methods of enhancing electrical activation of nervous tissue, incorporated by reference herein). In embodiments, the IPC is configured to be implanted adjacent to a target nerve approximately along the entirety of the IPC and with the length of the conductive element aligned with the length of the nerve (i.e. the dominant orientation of the nerve branch).

In an alternative embodiment, rather than conductive element 62 of FIG. 6A, the IPC in FIG. 6B is formed with a small or narrow gap 64 created within a non-conductive substrate 60. Not to be limited by theory, when the nerve target receives stimulation energy through the gap then enhanced nerve modulation may be obtained due to factors such as modified current density and edge effects (and possible increased phase synchrony) produced by the gap. It is hypothesized that the gap serves as a conductive window with respect to the larger non-conductive substrate 60 to modify the electrical field generated within the neural tissue (e.g., electric potential along the extracellular space of axons) that in turns enhances neural activation. There may be a single gap or multiple gaps created within a single substrate 60. Also, this mechanism may be implemented with a substrate 60 that has high electrical conductivity (e.g., 1000 times greater than saline).

FIG. 6C shows an embodiment of an implanted passive component comprising a first conductive component 62a and a second conductive component 62b that may be used to provide eTENS or eTMS. The first and second conductive components 62a, 62b have different conductivity levels such that energy which is transmitted within these two components encounters different levels of conductivity. Rather than being aligned in parallel, the passive conductive components can be oriented in series with respect to the target nerve or the magnetic field. Additionally, the two components 62a, 62b may be arranged with a gap therebetween, or be separated by a non-conductive element or diode. The energy signals may be electric or magnetic, such as provided by a magnetic stimulator. The magnetic stimulator is typically located outside of the patient. In embodiments, the two components are conductive rods that are each at least partially covered in a non-conductive substrate, and may only be exposed at their distal ends.

In embodiments, rather than relying upon the passive implants of eTENS that typically do not have electronics, the device 100 operates in conjunction with an active implantable component (or implantable neurostimulator) controlled by and powered by, for example, capacitive or inductive coupling, RF or microwave harvesting, or magnetic resonance. When implantable components are used that actively communicate data and/or power with external components using wireless technology for data/power such as Bluetooth, UI, or other protocol then the implant may be referred to as an implantable active component (IAC) and can contain coils, rectenna's and other components as is known in the art.

Features Module

The invention uses systems disclosed in U.S. application Ser. No. 15/678,824 disclosed previously by the inventors (incorporated by reference herein). FIG. 7 shows an embodiment of a system 68 with a device 71 having a power module 70 to provide power, a control module 72 for controlling the device 71 and other system components used in the provision of therapy, a communication module 74 for providing communication between system components (e.g. between the device and user/physician programmers) and communication over the internet/intranet using wired or wireless signals. The control module 72 includes processing circuitry, memory, computer readable medial and instructions, and timers as is well known. The device 71 also has a stimulation/sensing module 76 for providing the stimulation signals to the user via stimulators and for sensing data from the subject or from sensors such as accelerometers, motion detectors, optical and electrical sensors, etc. A user interaction module 78 allows interaction with users and the presentation of information to users. A feature module 80 provides a set of specialized modules which provide various unique features of the device 71.

In an embodiment, the feature module 80 operates pelvic floor management subroutines and content such as audio, text, and video-based instructions for use, pelvic floor exercises, lifestyle changes, the provision of stimulation therapy. The feature module 80 also operates to provide reminders related to activities (e.g. scheduled toileting) and the provision of therapy. The feature module 80 also provides tracking operations that allow for "use tracking", including calculation of energy provided (e.g., calculated as stimulation amplitude across time, and may be normalized to a level such as according to nerve recruitment or maximum comfort threshold). In order to deter against electrode "overuse" use may also be tracked using software that communicates via communication module 74 with a chip on the electrodes or electrode array that has a unique ID. This can occur in a wired or a wireless manner (e.g. RFID). The tracking algorithms may also be configured with purely time-based algorithms that wait an interval and then remind a user to replace one or more electrodes. Confirmation of this replacement may be requested, or automatically assessed. Alternatively, the stimulation/sensing module 76 senses impedance and evaluates the data to determine if the impedance level or variability of impedance is too high relative to a threshold. In the case the threshold is exceeded, the device 71 is configured to issue a warning to a user or halt operation until a stimulator with a new code is identified or otherwise confirmed. Measurement of electrode performance may be superior to measurement of number of stimulation sessions or total stimulation time due to differences in user behavior or environment. Users will vary in amount of skin oil, hair, and have different skin types all of which can affect device performance. Combinations of data related to time since last replacement, skin type, and impendence measurements may be used by the system to determine the proper interval for electrode replacement.

The stimulation treatment can be adjusted by the control module 72 to modify at least one brain or spinal cord feedback loop related to pelvic floor function and activity. The modification may be related to a brain or spinal cord feedback loop, and produce an immediate or delayed treatment response. When the modulation parameter adjustments are contingent upon assessment of changes in physiological activity the assessment may be performed on intervals during or near the time of stimulation, or may be computed upon intervals that occur several days or weeks after the stimulation. Since the effects of stimulation can extend past the stimulation period, both the delay and the duration of the changes can be assessed. The feedback algorithm may also operate upon data entered by the patient or caregiver.

In an embodiment, based upon an assessment of at least one measurement obtained during or after the assessment stimulation provided in step 10, an adjustment is made or is presented to the patient. This adjustment can be provided by an algorithm of the features module 80. The adjustment may include that the frequency or duration of stimulation should be increased when a measure reflecting benefit is not seen after an assessment interval. When the adjustment is proposed by a computer algorithm of a features module 80 or control module 72 of neurostimulator system, then the patient/user can accept or reject this proposed adjustment under operation of the user interaction module 78. Additionally, when a device is used at home and the patient provides feedback on symptoms or changes in symptoms, then instead of an algorithm assessing the data, a doctor at a remote location can assesses the user data and modify the system by remotely sending signals to a user device to change the stimulation protocol or to cause the device to present the suggested change to a patient. A patient device 106 (see FIG. 9) such as a smartphone that interacts with the patient to control a neurostimulator during the provision of therapy may prompt the user about the doctor's suggested change and user can accept or reject the change.

In embodiments, stimulation provided transcutaneously (or otherwise) may occur under control of the stimulation/sensing module 76 using a waveform of 200 uSec (0.2 msec) pulse width. This may range for example, from approximately 20 uSec to 100 msec. The pulses may be square waves or bipolar and may modulate frequencies of 1 kHz to 50 kHz or 100 kHz. The pulse waveforms may also have sinusoidal or other shape. When the pulses are square waves, these do not need to return to zero but may be offset so that applied is maintained between pulses. For example, the intra-pulse amplitude may be set at 50% of the difference between zero and the amplitude associated with nerve recruitment threshold.

In an embodiment a method, may comprise treating a disorder of a patient, including delivering initial electrical energy to neural tissue at an amplitude and at a frequency; receiving a first user input during treatment of the disorder that indicates perception of pain; receiving a second user input during treatment of the disorder that indicates perception of nerve recruitment; and adjusting the stimulation signal to be between the first and second user input. The adjusting the stimulation signal can include decreasing the amplitude of the electrical energy and increasing the frequency of the electrical energy to modulate the stimulation signal. The frequency of the stimulation signal can be at least 50 KHz and can also be above at least 100 KHz and this frequency can be modulated at a slower frequency of 1 to 30 Hz when stimulating the SAFN or PTN. These high frequencies can be continuous or be modulated at a lower frequency such as 20 Hz using square wave envelope which may be monopolar or bipolar envelopes. Further 50,000 Hz and 50,020 Hz signals can be used to create interference signals at 20 Hz. The initial electrical energy to neural tissue at an amplitude and at a frequency that is sufficient to cause the subject to indicate they experience a sensation related to saphenous nerve recruitment such as radiation along a nerve towards the foot or toe.

In an embodiment, the stimulation/sensing module 76 has a stimulation output circuit configured to deliver electrical energy to neural tissue at an amplitude and at a frequency to treat a disorder of a patient; and a controller/processor configured to respond to user input that indicates perception of nerve recruitment by setting the amplitude of the electrical energy and the frequency of the electrical energy at or slightly higher than that which prompted the response of the user. The delivered electrical energy comprises an electrical pulse train and the frequency is at least 50 KHz. The system can comprise at least two patch electrodes operably connected to the stimulation output circuit to deliver transcutaneous stimulation of the neural tissue to treat the disorder. The stimulation is of the SAFN and/or the TN and or Sural, peroneal nerve, vagus nerve, or nerve of the autonomic, parasympathetic, or sympathetic nerve. The system can also be comprised of monitoring circuitry configured to monitor an induced change (compared to prior to stimulation) in at least one of blood pressure, acidic concentration, or heat, and to automatically deactivate the stimulation output circuit if the induced change exceeds a threshold.

In embodiments, the amplitudes used during therapy provided by the stimulation module 76 (in step 22 of FIG. 2) can be selected in relation to the duration of the stimulation interval. For example, for sensory nerve stimulation intervals of approximately 30, 60, 90, 120 minutes the signal amplitude is set above recruitment threshold level as indicated by the patient experiencing a paresthesia radiating away from stimulation sites up or down the leg (for SAFN) and close to the level where a user experiences discomfort. If stimulation is provided for longer intervals such as for 240, 360 or 480 minutes, then the signal amplitude can be set lower to the recruitment level. Likewise, for the PTN the stimulation can be set at the high end of comfort level for shorter stimulation sessions and at lower levels closer to (or slightly above) foot twitch threshold for longer sessions. Additionally, if the stimulation is provided daily, then the stimulation amplitude may be made lower than if it is provided 1× weekly. Sufficient dose can be derived from a look-up table that may be part of module 244 (described later) and based upon a reference dataset such as age and gender matched population data.

In an embodiment, stimulation of the SAFN is provided at a first set of one or more selected times during the day having a stimulation parameter frequency shown to relax the bladder and decrease symptoms of OAB (or other pelvic floor disorder) in a patient (or population). At a second set of one or more selected times stimulation is provided to the SAFN or the PTN at a frequency shown to increase bladder activity to increase the likelihood of voiding such as at a time associated with scheduled toileting defined in a BBHM module 206 (disclosed later herein) or a time when the person determines they would like to attempt voiding. Toggling between an inhibitory and excitatory stimulation program occurs on a defined schedule, is user initiated by user input to a device 106 at times when the user would prefer to void, or both.

In embodiments, the assessment and tracking of treatment of disorders such as pelvic floor disorders (e.g., OAB) includes evaluation of symptoms, voiding, and also fluid and/or food intake. For example, a user who drinks 8 glasses of water per day may void more than during a period when they drink 4 glasses: the ability to increase fluid intake from 4 to 8 glasses of liquid without a corresponding increase in voiding or leaks can be assessed as a symptom improvement, and provides a context for assessing symptom change or lack thereof. Further, coffee may cause more frequent voiding, or quicker voiding from time of consumption, than water due to its diuretic properties. Accordingly, the feature module 80 (see FIG. 7) includes a tracking subroutine that tracks the type of beverage consumed as well as amount.

This data is entered into the system either by using sensors (sensors incorporated into a cup which sense, store and transmit beverage consumption statistics), electronic bladder diaries, or by the the user interaction module 78 presenting relevant questions to users ("how much liquid did you drink today?") which may be recorded using paper or electronic means such as a smartphone, tablet or other computing device (e.g., a specialized external device (EXD) or realized as a data input and remote control device). In an embodiment, if evaluation of data shows a symptom worsens (e.g., increased occurrence of nocturia) on one or more 24 hours periods relative to a recent history (e.g. 1 week or month) then the system prompts the user with a question such as "did you drink more than typical yesterday?", "is there a reason that bathroom trips at night are increasing?", "did you forget to take your OAB medication recently?" etc. The answers to these questions are stored and may invoke additional questions or request the user make selections from multiple choice items about a topic. This allows a change in voiding or symptoms to be correlated or contextualized with user behaviors or conditions such as changes in consumption or stress. Additionally, the system is configured to prompt a user to answer questions such as "are you are able to retain urine for longer periods compared to before therapy started?". The therapy regimen may be adjusted (or therapy changes may be suggested) manually or by algorithm depending upon the answers to various sets of questions. The questions may also relate to urge severity, speed of onset, or, in contrast may be related to a lack of sensation/awareness of voiding such as urination. Although urge or urge incontinence may be more typically treatment by stimulation, stress incontinence can be assisted as well, and the stimulation can be combined with other therapies such as fillers, surgically implanted meshes, etc.

In an embodiment, a portable device which is a wearable stimulator provides transcutaneous stimulation of a first nerve and a second nerve (e.g., SAFN and PTN). Alternatively, stimulation is provided at 2 or more locations of the same nerve. When the system has both external and internal components the implanted device provides a first therapy, which may be a basal level of therapy. This is complemented by external stimulation to improve benefit. This is advantageous if the implanted device therapy is insufficient, or during the induction period when more frequent or longer stimulation occurs. If internal and external stimulation is applied to a different target nerve (or same nerve on a different leg) unwanted effects such as habituation can be deterred. The internal and external stimulation can be user initiated or guided by a treatment schedule defined in the control module 72.

External stimulation may be applied in patients without implanted components, or in patients with an implantable device. Ad hoc, external stimulation may be provided as a complement to any scheduled (implantable) therapy due to an acute need such as increased symptoms during a period (a day or week), or at night (in the case of nocturia). If the implanted stimulator has limited battery then external stimulation (provided in a complimentary manner, as a substitute, or at a higher stimulation amplitude) can extend battery life. During an induction period, external or internal stimulation can be provided continuously, or alternatingly such as 4 hours on/4 hours off, periodically (e.g. for N hours every other day), or according to a customizable schedule. The schedule may be updated and adjusted based upon patient input to questions and/or data about changes in symptoms, incontinence, use of incontinence products (e.g. not using on a particular day), a period of increased anxiety or stress, or due to lifestyle or consumption behavior (e.g. drinking more coffee on weekdays), or other factors.

In an embodiment, the portable device 100, which may wearable, has components and securing means that is adjustable for various sizes, nerve targets, and stimulation locations. A device intended for use near the ankle area may be sized for a smaller range of anatomy than one configured to stimulate at or near the knee area, or area of the upper leg such as a thigh region.

In an embodiment, the device 71 uses a communication module 74 to communicate with a computer network 82. A "computer network" refers to a network of computers such as may exist in a hospital or other medical care facility, in a doctor's clinic, in a managed care community, or which includes computers at remote locations such as patient's home. Network computers are configured for communication across the internet or an intranet using wired, wireless, WIFI, and cellular communication networks. The networks may include secure networks such as a hospital network. Data can be analyzed and communicated with computer or device associated with the network so that network information is managed in distributed manner.

In embodiments, the computer network 82 communicates with the systems and devices disclosed herein directly or via relayed communication from intermediary computers or electronic devices. The computer network 82 has all the hardware, processors, memory, communication protocols and hardware required for multi-computer communication, as well as computer readable code, associated media, and software instructions generally understood to allow networks to function. Patient devices 106 such as smartphones with software applications used during provision of therapy (which serve a patient programmer or interface device that allows the patient to interact with the device and network) are considered part of the network.

In embodiments, the system 68 is used in a hospital or community care setting. Any device or system component (e.g. electrode array) used to provide care is configured with a unique ID code, which in turn is linked to a patient or room and allows tracking of resources and treatment. A central monitoring station (e.g., nursing station 114) is configured with monitoring/tracking software that allows monitoring and determination of treatment compliance for a treatment schedule. It is configured to display compliance data and notify a patient or caregiver to non-compliance if the data do not meet a compliance criterion. The system 68 may also use electronic sensor technology (e.g. moisture sensors) in garments (such as the Sensassure™ system Toronto, Ontario, WO2016090492, entitled impedance sensors for detecting and monitoring moisture in absorbent articles;

WO2017EP66607, entitled sensing device and charging system, both incorporated by reference herein) which allows for automated and remote incontinence monitoring and management. The system 68 is configured to adjust the treatment protocols or stimulation parameters used by an external or internal neurostimulator contingently due to assessment of data by the system 68, flag or suggest such an adjustment for review by a nurse, doctor, caretaker, or simply collect and display result data and trends related to moisture levels and durations.

In embodiments, the system 68 includes a blood pressure sensor, or can communicate with a blood pressure or other sensor that measures change in blood pressure, heart rate, blood gas, or other cardiovascular measure over time. Cardiovascular data can be used to assess pressure periodically during treatment (to monitor the progress of therapy), and both before and after a session of stimulation to measure the stimulation evoked changes.

In embodiments, the device 71 utilizes one or more straps, frames, adhesives, elastic bands, and other attachment means to secure system elements to a patient. System 68 elements can include the neurostimulator 71, stimulators, patient controllers, and/or sensors and realized as a portable, wearable, and/or disposable, or with specific disposable components. External system components can use electrically conductive hydrogels or pastes with the stimulators to increase conductivity. The components are also realizable through incorporation of dry electrodes and/or conductive fabrics (e.g. silver coated). Although a commonly used configuration for SAFN stimulation is likely a device configured to be attached to the upper calf, in alternative embodiments system elements are designed for attachment to a user's ankle, thigh, or foot. In embodiments at least a portion of garment material is realized using elastic and/or compressive material. When compressive materials are used the design may assist with biasing a stimulator towards the target nerve and push away intervening tissue.

In an embodiment, as shown in FIG. 8 at least one percutaneous lead 84 is percutaneously position (or implanted) in a patient's leg 86. This may be used for treatment that lasts for approximately 30 to 90 days. The lead travels through a lead interface 90 on the skin of the leg and is connected to an external neurostimulator 88 that is secured to the patient. Such a system has been developed by SPR Therapeutics and disclosed in US patent publication US 20140121741 entitled "Systems and methods to place one or more leads in muscle for providing electrical stimulation to treat pain" and U.S. Pat. No. 8,249,713 entitled "Treatment of shoulder dysfunction using a percutaneous intramuscular stimulation system", and these are incorporated by reference herein. In the systems of those two references, an external programmable neurostimulator is connected to the percutaneous lead through the interface 90 and is inserted to treat pain. In an embodiment, rather than a single lead 84, the an external conduit may route the signal from the neurostimulator to the interface 90 and an implanted lead may route the signal to the nerve.

The present invention may apply such a wearable medium-term percutaneous system 83 to the treatment of pelvic floor disorders, or other disorders. When the nerve stimulation occurs using a nerve in the leg such as the SAFN and/or TN nerves, then the percutaneous lead is positioned for successful stimulation of these targets. The positioning of the lead and adjustment of stimulation parameters may be assessed using methods which have been disclosed herein (e.g. FIG. 1). In an embodiment this system can be used during a screening or assessment interval which may precede treatment with a different device (implantable device or TENS) by assisting to determine positive and negative responders in candidates for these other modes of therapy. For example, correct positioning and treatment provision may require that a patient continue to be able to subjectively report sensations associated with successful nerve recruitment—the percutaneous device can be used to confirm this over time. Use of a medium-term percutaneous system, can be used to assess treatment response of a peripheral nerve stimulation for treatment of pelvic floor disorders, urological disorders, sexual disorders, and may also be used for assessment of disorders related to hypertension, or disorders of the autonomic nerve system. Successful treatment-response can be seen in measures related to sympathetic or parasympathetic activation (associated with relaxation-contraction related to micturition), heart rate, heart rate variability, blood pressure, etc.

In embodiments, the systems and methods of the current invention include using one of at least transcutaneous, percutaneous, implanted, or eTENS stimulation. In other embodiments, a combination of these stimulation types is used to provide a selected interval of stimulation. In embodiments that disclose using external stimulation to complement stimulation provided by an implanted device, are understood to include percutaneous stimulation provided by an external neurostimulator.

Figure 9:
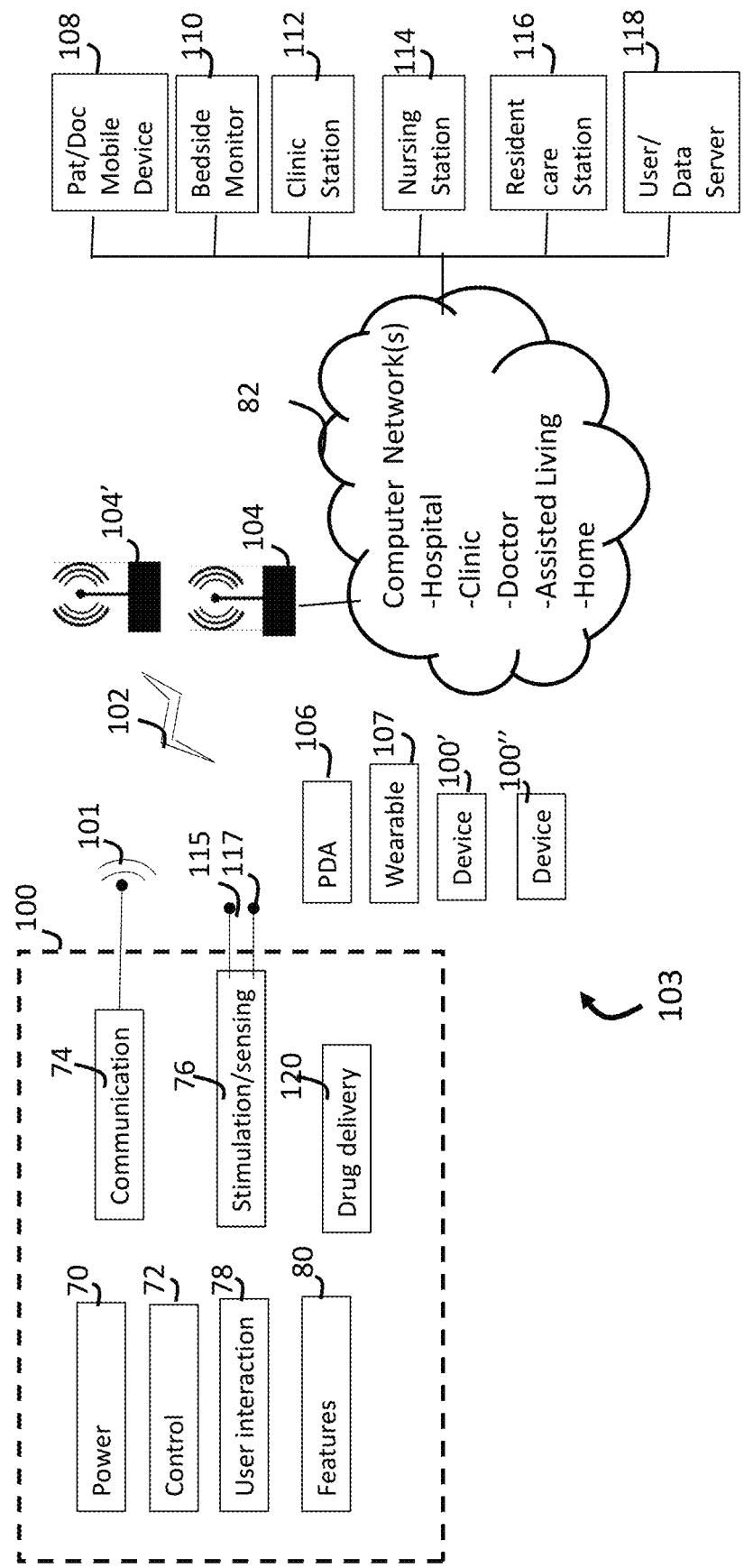
FIG. 9 shows a system for providing therapy to one or more patients with a least one treatment device and a computer network at least partially realized with components in a hospital, clinic, or other location.

FIG. 9 shows an embodiment of a system 103 including a stimulation device 100 configured for providing therapy and communicating with both local (e.g. in a patient's room) and remote (e.g., outside of the room) system components. In an embodiment, the device 100 communicates directly with a computer network 82 using its communication module 74 and wireless transceiver 101 which sends a signal to a wireless communication device 104. The network 82 in turn communicates with a remote system component. Alternatively, the device 100 communicates with a patient programmer 106 which then relays data to the network via wireless access point 104. The device 100 has an electrical stimulation and sensing module 76 to stimulate a user and sense data related to a user (not shown). The sensing allows user monitoring by the device and/or by medical devices and sensors that can obtain sensed data, such as physiological measures. Sensed data can include electrocardiographic (ECG) data (e.g. heart rate/variability (HRV) and blood pressure), such as from ECG electrodes, optical sensors, blood pressure cuffs, accelerometer data, electrical data related to muscle or nerve activity, etc. The ECG data can be obtained by an instrument with ECG electrodes which is then communicated to the device 100. A wearable 107 such as wrist-worn medical device can be configured to monitor, for example, blood pressure, blood oxygenation (SpO2), pulse, or physiological measures and can also communicate with the device. The patient programmers 106, can be wearable devices such as smartwatches and fitness tracking/health monitoring bracelets that are provided with software applications that enable communication with the system 103, or these can be customized wearables that are provided with buttons for user interaction, sensors, and alerting capabilities for vibration, sonic, visual alerting. Ear stimulation/sensing technologies can also be used to sense brain, cardiac, temperature or other data and to communicate with users. The device 100 can also communicate with one or more wearables 107 which can be at least one device worn by a patient on their body such as wrist, leg, or other body worn device. The wearable can allow interaction with the user and also may monitor blood pressure, blood oxygenation ($SpO_2$), pulse, temperature or other data. Sensed data for user monitoring can relate to data related to patient health, activity, consumption, voiding, or other aspect of the user. The stimulation device 100 can control and communicate with sensors or devices such as wearables 107 to provide stimulation or sensing through module 76 and can communicate through the communication module 74.

The device 100 includes a power module 70 for powering the device, a control module 72 for controlling the device as well as other system 103 components used to provide therapy, a user interface module for communicating with a user and accepting user input data, and providing alerting signals. The communication module 74 for transmitting and receiving data signals in a wired or wireless manner (i.e., via a wireless communication signal connection 102) between itself and devices such as a wearable 107, a patient programmer (e.g., personal data assistant) 106, or at least one router/modem such as a wireless router 104 that serves as a wireless access point (WAP) that allows the device 100 and other system components 107 access to a wireless local area network (WLAN) to communicate with each other, the internet, or a computer network. While one transceiver 101 is shown, more than one can be provided to communicate using different technologies. While a second wireless access point 104' is shown, there may be tens or hundreds in a hospital and multiple WLANs can be connected, as is well known. Additionally, while one network 82 is shown many can be distributed to provide desired coverage area. A computer network 82 such as a hospital network can allow data communication between the device 100 and other system components such as a user/data server 118 where the data can be processed, stored, displayed, and relayed forward to other system components. For example, data signals 102 can be transmitted through the network 82 to a patient or doctor mobile device 108 such as smartphone or wearable. Data can also be displayed for a medical technician or nurse who may review or be alerted to patient data via a bedside monitor 110 or at a nursing station 114. The data may also be relayed to a central monitoring station, a doctor mobile device 108, or the like. When used in a clinic, the data can be transmitted from the device 100 wirelessly to a wireless communication device 104 and through at least one network 82 which may include a user's home computer network and a clinic computer network so that it can be provided to and operated upon by the clinic station to allow viewing, processing, etc. The clinic station may also allow a doctor to adjust the operation of the device 100 remotely. Information can also communicated between the device 100 and a resident care station 116 when the device is used in an assisted living/elderly care setting where patients live in single building, multiple houses, or within a physical or virtual community which receives assisted living care. While only one nursing station 114 is shown, obviously the information can be shared across multiple nursing stations. The device 100 can communicate with a wearable 107 such as a smartwatch to send the user reminders about providing treatment. Although a solid set of lines shows connections from the computer network 82 to various system components such as the bedside monitor 110, this can occur in a wired, wireless, or indirect manner.

In an embodiment, the user/data server can be incorporated into, or share data with, an electronic medical system that tracks data related to a patient. Accordingly, when the system is used for providing OAB patient monitoring a nursing station may display information on each of a set of patients which includes data such as: number of treatments a patient provides each week, what day the treatments are scheduled on, average number of voids per day, weekly number of diapers used, weekly number of linen changes due to voiding, any incidence of daytime or night time falls related to seeking the toilet, bed sores, urinary tract infections, cardiac activity measures such as blood pressure and heart rate variability, medication type and dosage, and other information related to the patient's health which may be collected by a care or service provider. Additionally, "asset tracking" technology, can be provided in the bedside monitor or device using, for example, optical scanning or RFID technology to track information. For example, when an adult incontinence product is used, its serial number may be scanned into the bedside monitor or a user may provide input indicating a product has been used. If a device 100 is used on more than one patient then it may communicate with the bedside monitor so that either the device 100 or user/data server can update the information which maps the use of the device 100 with a particular patient.

Data can be communicated using one or more communication channels that use, for example, Bluetooth, a shared wireless channel using IEEE 802.11 (which may include including quality of service (QoS) extensions, 802.11e, IEEE 802.16/WiMAX, and obvious variant technologies, as well as communication schemes such as using "ACK messages" when system components receive information from other components), Wi-Fi network technology, cellular networking or broadband wireless access technologies, a specific band of radio frequency or a communication protocol. The selection of a communication channel could be performed by user configuration or it could be done dynamically in a system. One or more channels used for Zigbee or Bluetooth radios can be used with communicating protocols using one or more predetermined duration(s) and location(s), beacon time limits which relate to channel failure, etc. as is well known. Should transmission of data not occur successfully (defined using communication criteria such as number of communication attempts or duration of attempts) then an error message (e.g., visual/sonic/text signal) can be provided to a component of the computer network or to the device 100, or system component such as an interface device 106.

The device 100, WAP 104, computer network 82, the user/data server 118, wearable 107, and any other system component include a the necessary memory (e.g., RAM, ROM, PROM, EPROM, FLASH), realized as a memory chip or other computer-readable medium for storing computer executable instructions to be operated upon by one or more processors to execute computer-executable instructions for performing the operations, functions, steps, methods, etc., described herein. The system and network components can be realized, in part using customized remote controllers or smart devices (e.g. PDA 106), one or more general purpose computers or special purpose computers (e.g., a server or group of servers working together).

The system can be integrated obtain data from the electronic medical records (EMRs) of a patient which can be implemented as part of, or shared with, the User/Data Server. The computer network and wired/wireless communication can include or incorporate an internet-accessible wireless communication network, and preferably, over a wireless wide-area network (WWAN) such as a mobile telephone data network including (for example, based on a Global System for Mobile Communications (GSM) or Code Division Multiple Access (CDMA) cellular network or associated wireless data channels). For compliance with medical regulations, for example HIPAA, communication across the networks are preferably conducted securely.

Although a main focus of the system 103 is for the provision of treatment of pelvic floor disorders, the treatment device can be a portable or wearable device that is related to the treatment of many other types of disorders or conditions including addiction such as smoking, drug/opioid abuse, blood pressure, cardiovascular, metabolic or psychiatric disorders, migraine, headache, sleep, sleep apnea, stroke, cognitive, movement disorders including tremor and Parkinson's. Various wearable stimulators may stimulate various limbs of the body or nerves such as the vagus or cranial nerves, and can be managed within the system 103. Devices which may be designed to stimulate locations which have been found to create desired changes using acupuncture or electro-acupuncture can be incorporated into the system 103 and are considered within the scope of the claimed invention. These also include devices configured to modulate inflammatory response, cardiac activity, or appetite of an organism, and other conditions treated by "electroceuticals".

The methods and systems of the current invention can be used to modulate physiological activity such as the frequency, pattern, and/or size of urologic, bladder, gastrointestinal, or rectal activity/micturition contractions. The pelvic floor disorders that may be treated, for example, include: OAB symptoms, bladder overactivity, fecal/urinary incontinence (including bedwetting) and nocturia, interstitial cystitis, urinary retention, pelvic pain, irritable bowel syndrome, constipation, and sexual dysfunction.

According to any aspect described herein, with electrical pulses at a frequency and amplitude able to either inhibit one or more of bladder contractions, rectum contractions, urination, defecation, and pelvic pain of the bladder, urethra, prostate, anus or rectum, thereby obtaining the physiological response. The physiological response may be one or more of inhibition of micturition, defecation, bladder contractions, pelvic pain of bladder, urethra, prostate, anus, or rectum, and inhibition of rectal contractions.

A computer network 82 such as a hospital based system provides a central dashboard realized in a nursing station 114, which communicates with a set of devices 100, 100' etc. which can be used by different individuals or one device can be mapped to several patients. For example, mapping occurs by scanning a code on a patient's ID bracelet, entering a patient ID, or in other manners that provide for patient anonymity and correspond to HIPPA guidelines. Device-to-patient mapping also use digital signatures, RFID tags, or Internet of Things (IOT) technologies. Communication between system components can occur using a cellular network, the internet, or a wired, wireless, or mixed network which may include hotspots (wireless access points), WIFI, Bluetooth, and other wireless technologies and communication protocols. The device 100 can have at least one wireless or wired communication module 74 that has necessary circuitry to provide for communication and uses at least a first transceiver 101. When the device 100 transmits data to a local wired or wireless access point 104 this can then be transmitted over the network for access by a doctor's mobile device 108, a nursing station 114, a patient bedside monitor 110, or a patient information server 118 located remotely. The communication can include handshaking (e.g. ACK) and login/password protocols to a secure network.

In an embodiment, the system provides monitoring of stimulation usage, of patient input, of data related to a patient's medical or physiological condition, and sensor data from a sensor related to moisture or motion. The system can be realized in an intensive care unit, a hospital, a residential/assisted living center realized in one building or distributed across several buildings or across geographically distant regions. The transmitted data of a patient can be displayed on a bedside monitor 110 so a caretaker has access to relevant medical data such as treatment/compliance history in relation to an individual's neurostimulation schedule. The bedside monitor 110 or user/data server 118 containing patient information can be configured to alert a caregiver when a treatment is scheduled (i.e. "Patient X has a scheduled stimulation treatment today") or to compliance issues (i.e. "Patient X missed two treatment sessions in the last week"). The analysis of patient data by any system component (e.g. 118) can indicate whether the patient's data or condition warrants generating 1 or more types of visual, sonic, or other type of alarms. If wired or wireless communication is deemed unavailable (e.g. communication has not been achieved for 2 days) the device 100 (and/or external neurostimulator or PDA 106) can be programmed to store this information in memory. Rather than a TENS device 100, an implanted neurostimulator may be used, which relies on an external device which may be a wearable device 107 to control therapy. If implanted neurostimulators are powered/controlled by external devices, then the system is configured to communicate with these external controller devices. When an external or implanted neurostimulator is powered wirelessly by a wireless power network, prior to the network supplying power to provide stimulation, the system may be programmed to signal the patient and further to receive a response so that the stimulation does not occur unexpectedly. The system can be integrated with a network 82 that uses a third-party system that supports voice services (e.g., Echo™ or Alexa™) permitting vocal interaction between system and the user as part of therapy.

Pharmaceutical Applications

In an embodiment, the system 103 incorporates drug delivery for medical disorders. For example, drug delivery module 120 has pumps and controllers located within the device 100 housing or the device 100 communicates with and/or controls drug delivery devices that are part of module 120. Suitable delivery devices include micropump devices (implanted or external), percutaneous, or dermal delivery system (e.g., with pressure, iontophoresis, or other means of delivery) to provide therapy alone or in combination with electrical therapy regimens. Further, manual drug delivery, oral/nasal sprays, or parenteral drug administration and delivery of time-release technologies may be accomplished through patient notification.

Example embodiments of systems and methods related to the system 103 of the current invention are integrated with drug delivery systems such as US 20120253263 (entitled Two-Part Electrotransport Device), US 2017023946 (entitled Electrotransport drug delivery devices and methods of operation), and US 20160220798 (entitled Drug delivery methods and systems), US 20140046240 (entitled Electronic assembly for iontophoresis transdermal drug delivery and device thereof), and U.S. Pat. No. 9,327,114 (entitled User-activated self-contained co-packaged iontophoretic drug delivery system), which are incorporated by reference herein for all purposes.

Delivery can use technologies such as transdermal microdispensers (e.g., Omnipod system) that can provide smart delivery and communicate with (and controlled by) mobile devices to deliver prescription or over-the-counter substances (e.g., vitamins or caffeine). Delivery may use microneedles, iontophoresis, electroporation, ultrasound, transdermal pumps and smart patches.

A transdermal, percutaneous, cutaneous, subdermal, implanted, desktop or wearable device may be operated by the system 103 to provide drug delivery. The drug delivery module 120 can integrate biologically-timed drug delivery with reminder alerts, compliance tracking and personalized digital support that is realized near the patient and/or remotely. Parameter values related to drug or electrical "doses" can be set which relate to permitted drug or stimulation amounts (amplitude, number of treatments per unit time, drug dose, etc.).

Lifestyle and Compliance

In the treatment of OAB or other medical disorders, states, or conditions behavioral support is be provided by a feature module 80. In embodiments, features module 80 is realized as part of a compliance module (not shown), and includes software modules, media, and content for providing behavioral coaching, tracking, and prompting for various types of physical exercises (e.g., Kegel exercises). These features include videos or graphic animation that provides instructions and content. The software can provide connection for online chat or video support such as technical support or counselling. This can also be supplied via a link to a website which provides these services through a web browser. In the treatment of OAB, symptom and fluid intake tracking can be provided by a PDA 106 to track and measure this and also to relate this to amount or timing of voiding (i.e. the features module can be realized in part within the PDA 106 or wearable 107). Fluid intake and voiding can be recorded, for example as an electronic bladder diary. Virtual behavior coaching associated with first line therapies can also be provided such as providing nutritional and/or fluid recommendations and reminders. Videos and instructions can also be provided for pelvic floor exercises. Further, various support features can also be provided such as the ability to have physician referrals or referrals to virtual support groups (i.e. chat groups/discussion boards). Stimulation protocols can be tied to various aspects of the therapy such as turning on electrical stimulation if user input suggests this is merited or desired.

If a user stops providing at-home therapy then there is considerable value in understanding what prompted this. The features module 80 can operate a non-compliance protocol termed a "stopped therapy" protocol which evaluates the reasons for complete care termination. In an embodiment, the user is sent a notification on the patient programmer 106 which alerts the patient to non-compliance. In an embodiment, a message such as "You have stopped using your device for at least X days" or "you have selected 'ignore' the last x-times when notified to start therapy". The notification can be followed by a first set of user input choices related to halting treatment. Is this due to: A) a problem; B) Change in symptoms; C) other. A second set of user input choices will be invoked depending upon the user input response to the first set of choices. For example, if the user selected "A" then the protocol would as the user to select from a plurality of reasons such as: A) skin irritation B) pain at stimulation site C) cost of treatment, and D) other. For example, if the user selected "B" then the protocol would as the user to select from a plurality of reasons such as: A) symptoms got worse B) symptoms did not change C) symptoms got better, and D) other. For example, if the user selected "C" then the protocol would as the user to select from a plurality of reasons such as: A) switched to a different therapy B) instructed by Dr. C) On vacation D) sent back device. In an embodiment, additional questions can be proposed to a user based upon the answers to the second set of user input choices.

Closed Loop and Guided Therapy

In embodiments, the device 100 and system 103 is configured to provide therapy based upon evaluation of data, sensed data, or a signal serving to provide feedback. The feedback data is real-time or recent data, such as recent sensor data or user input, or includes historical feedback data. For example, if patient input indicates symptom improvement then the therapy duration or number of treatments per week may be adjusted to decrease. Alternatively, if a trend of increased benefit levels off or decreases, then the therapy may be adjusted to increase. In an embodiment, the treatment adjustment rules for operating upon feedback data lead to outcomes based upon whether or not the data meet one or more therapy criteria. The therapy criteria can operate upon single values of feedback data, or upon summary statistics or trend statistics.

In an embodiment, a portable device 100 for treating OAB symptoms in a patient includes a patient programmer 106 configured to provide communication and control of the portable device 100 to control a stimulation & sensing module 76 to provide a first electrical stimulus to the saphenous nerve and provide a second electrical stimulus to a lower limb nerve according to a stimulation protocol having parameters configured to treat overactive bladder symptoms. The first stimulator is connected to a stimulus generator of the stimulation & sensing module 76, and comprises at least one transcutaneous electrical nerve stimulation pad having at least one conductive element 46a configured to be positioned to modulate the SAFN. Additionally, a second stimulator, comprises at least an electrical nerve stimulation electrode configured to be positioned to modulate a lower limb nerve such as the sural, peroneal, or tibial nerve. In an embodiment, cutaneous nerves on the medial aspect of the leg at or below the area of the knee may be stimulated.

The device 100 can further comprise at least one sensor connected to the stimulation & sensing module 76 for obtaining sensed data and a communication module for allowing patient data input. The sensed data or patient data serves as feedback data and the device control module 72 comprises a processor that is configured to operate upon the feedback data to evaluate the feedback data and to cause the device to adjust one or more parameters of the stimulation protocol of the first electrical stimulus and the second electrical stimulus based at least in part on the evaluation of feedback data. The processor is further configured to provide the first electrical stimulus to the saphenous nerve and provide the second stimulus to the PTN.

The device 100 can provide a second stimulator which is transcutaneous and is connected to the stimulus generator or alternatively the device 100 can communicate with an implanted pulse generator that provides a stimulation signal to a second stimulator that is implanted adjacent to a nerve in the lower limb such as the PTN. The implanted pulse generator is configured to communicate data and receive control signals with the external controller of the device 100 or a patient programmer 106. The feedback data can include electrical activity related to muscle or nerve activity of the patient or other sensed data such as cardiac data, or other data such as that which is sensed by an electrical or optical sensor. The feedback data cab also include patient input data input by a user via the user interaction module 78, which is related to overactive bladder symptoms, urinary urgency, urinary frequency, urge incontinence, and subjective scores related to voiding, sexual dysfunction such as sexual desire or erectile dysfunction.

In an embodiment the pulse generator is configured to generate pulses of between 1-100 V and 1-100 mA, having a pulsewidth of 0.01-3 msec, and a frequency of between 0.1 to 50 Hz, and the stimulation parameters of amplitude and frequency can be set to cause an increase or decrease in bladder activity. The pulses can be monophasic, rectangular pulses or biphasic.

Placement and Confirmation of Implanted Stimulator

In an embodiment, a method of implanting at least one of the devices 100″ (of FIG. 9) in the lower limb of the user, include the step of positioning a first stimulator on a housing of the at least first neurostimulator device 100″ and implanting the device at a position proximate and posterior to a medial malleolus of the patient. The location may be adjacent to a portion of the SAFN of the patient and also adjacent to a portion of the PTN. The neurostimulator device 100″ is configured to provide stimulation using at least two electrode contacts on at least a first stimulator using at least a first stimulation signal having a selectable amplitude that is sufficient to provide concurrent stimulation of the PTN and at least one branch of the SAFN. The branch of the SAFN can be located superficial to the PTN. In an embodiment, the stimulator is positioned under the skin, inside the fat, but above the fascia and does not require dissection of the muscle or fascia/deep fascia overlying the PTN to modulate the PTN. The incisions can be through the skin and the implant is placed superficial to the deep fascia, between the deep fascia and the skin. For example, the neurostimulator 100″ can be adapted to be positioned adjacent to a portion of the SAFN of the patient for providing stimulation at a location that is cephalad to the medial malleolus and posterior to the saphenous vein at a displaced distance within the approximate range of 0.5-2 cm to be adjacent to a portion of the PTN, and at a subcutaneous depth approximately above the deep fascia within the approximate range of 5 mm and 1.5 cm.

The signal is adjusted to be sufficiently strong to stimulate the SAFN, PTN, or both. In this embodiment, the position and stimulation amplitude are determined appropriate for stimulating at least the SAFN by obtaining confirmation from the implanted individual that he/she can sense nerve recruitment at a site that is not adjacent to the electrode. For example, a vibrotactile or cutaneous sensation (e.g. paresthesia) should be detected along the medial aspect of the leg at a site between the stimulator and the knee. Alternatively, confirmation of a successful implant location and/or stimulation parameters can include objective measures of stimulation-evoked changes. The changes can be recorded from the medial aspect of the leg, or from the SAFN/tibial nerves located at or below the knee.

The change can be related to a measure of sensed nerve activity recorded using a percutaneous or cutaneous sensor. In an embodiment, the sensed electrical activity may be evaluated as a time-locked average response which is collected using pulsed stimulation as a trigger. Accordingly, a patient/physician programmer, realized as a PDA 106, can transmit control signals to the implantable stimulator to cause it to provide a stimulation signal while also recording from a sensor in a time-locked manner to assess time-locked evoked activity. In some patients, a muscle-evoked response may also be seen in the thigh or foot during SAFN stimulation, and this may be due to spillover co-activation of other nerves.

In an embodiment, the neurostimulator is realized with a coin form factor with two electrodes on its ventral surface, an electrode on the ventral surface and a ring electrode around the perimeter. In an alternative embodiment, a neurostimulator with a coin form factor may have at least one electrode on its top surface to primarily stimulate the SAFN and at least a second electrode stimulator on its bottom surface to primarily stimulate the PTN, and the device is implanted between the two nerves.

In an embodiment, a method for modulating voiding activity of a patient comprises the steps of implanting an electrode (which may be on the body of a neurostimulator) cephalad (e.g., 3-5 cm) and posterior to the medial malleolus and applying a stimulation signal from the implanted electrode while the electrode is closer to the SAFN than the PTN. If the electrode is multipolar, or the electrodes on the body of a neurostimulator are configured adjacently, then the stimulation protocol can use field steering and the method may include using multiple contacts to steer the field towards at least one of the SAFN target PTN target, or both.

The system 103 may have only external components or may have only external stimulators such as occurs with TENS, or the stimulators may be only percutaneous, or may be only implanted, or stimulation can be provided in a system realized as a combination of these three different stimulation types. When the stimulator is an implanted electroacupuncture device, it may operate using an implanted battery and may be operate after an initial programming session that sets the stimulation protocol for the patient. In an implantable embodiment, the stimulator does not have to be provided below the knee and can be positioned within the leg at or below the level of the head of the femur. When the stimulator is positioned to primarily modulate the saphenous nerve this may more typically occur at or below the level of the knee, but locations adjacent to the medial malleolus, and even within the foot are also possible. When the stimulator is positioned to primarily modulate the PTN portion of the tibial nerve, the positioning is typically near the medial malleolus.

In an embodiment, a system 103 for providing stimulation of a pelvic floor disorder comprises at least a first stimulator set 115 including at least a first stimulator which is externally or percutaneously positioned for stimulating at least a first nerve which is the saphenous nerve according to a first stimulation program provided by a first pulse generator of at least a first external neurostimulator device and at least a second stimulator positioned for stimulating at least a second nerve, which is a nerve of the lower limb, according to a second stimulation program, the second stimulator being implanted and connected to a second pulse generator of at least an implanted neurostimulator 100″. At least one patient programmer 106 is configured for controlling at least one of the first and second neurostimulator to provide the first or second stimulation program that is configured with stimulation parameters for modulating a pelvic floor disorder, whereby stimulation can be provided at least one of externally, internally, or in combination. The at least a first nerve is the saphenous nerve and the at least a second nerve is the tibial nerve. Alternatively, the at least first and second nerve include at least the saphenous nerve. When the implantable neurostimulator uses a non-rechargeable battery then the external stimulation may be supplied to provide additional stimulation which does not use up battery power, or the additional stimulation is provided to increase the therapy benefit or provide other advantage over that which the patient experiences using only the implantable. For example, this may increase the therapy benefit over that which the patient experiences using only the implantable, wherein the therapy obtained using the implantable alone does not meet a therapy threshold. In an alternative, the external and implanted stimulator primarily stimulate at least the same nerve, such as the saphenous nerve, or the external and implanted stimulator are positioned to primarily stimulate two different nerves. When stimulating the saphenous nerve, the stimulation parameters (e.g. amplitude) are set at least at a level that produces nerve recruitment sufficient to cause a sensation to radiate down the leg from a stimulator positioned below the knee, or at a level that produces nerve recruitment sufficient to cause a sensation to radiate up the medial aspect of the leg below the knee from a stimulator positioned near the medial malleolus, such as a location approximately 1 to 5 cm caudal and also posterior to the medial malleolus. The frequency parameter of the first or second stimulation program can be set to between 0.5 Hz and 50 Hz to modulate bladder activity to improve OAB symptoms of a patient. The at least one controller 106 of the system 103 can be configured for controlling both the first and second neurostimulator to provide both the first and second stimulation program according to a treatment regimen defined for the patient which includes the provision of stimulation using at least one of the implanted and external stimulator. The internal and external stimulation protocols can be implemented and adjusted as two separate stimulation programs, and the adjustment may be made independently for either program. Additionally, an advantage may be obtained when the implanted neurostimulator 100" provides scheduled and/or periodic stimulation while external neurostimulator 100 provides additional stimulation to supplement internal with additional stimulation or in an on-demand manner to address, for example, acute symptoms of a patient. This may be an advantage, for example, if the implanted neurostimulator 100" uses a non-rechargeable battery to provide the advantage of decreased device cost and complexity compared to rechargeable.

Patient Management Platform (PMP)

Figure 10:
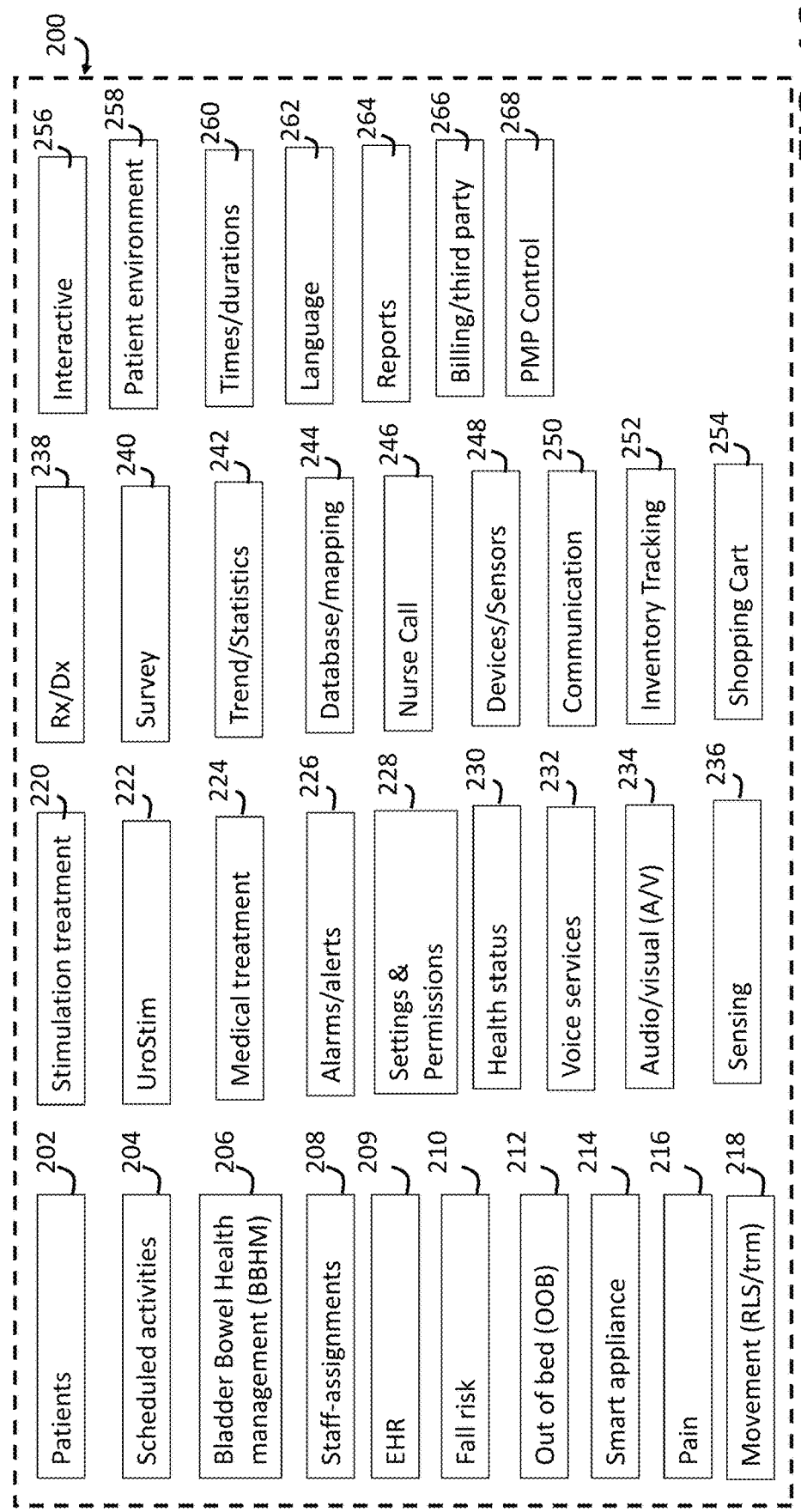
FIG. 10 shows modules of a patient management platform (PMP) system which is used to manage treatment for one or more patients with a least one treatment device typically in conjunction with a computer network at least partially realized with components in a hospital, clinic, or other location.

FIG. 10 shows the EBT patient management platform (PMP) 200 which is a system that provides a preventative and active approach healthcare and patient/resource management. The PMP is a connected health platform which preferably incorporates interactive technology designed to improve patient health, satisfaction and coordination of care. The PMP promotes overall patient health, and provides features that assess, track, and improve pelvic health. For example, treatment and management of OAB should decrease rates of nocturia (waking at night for voiding) and enuresis (bedwetting) which contribute to falling (and resulting fractures) and urinary tract infections (UTIs). The PMP allows savings of time, streamlining and automation of workflow, reduction in "nurse bell" occurrence and corresponding nurse-response delay. PMP accuracy is maintained by interaction with the hospital electronic health records (EHR) system and sensors that provide updated information about the patient and environment.

Bladder and bowel activity (BBA) information that is operated upon by the PMP includes, for example, history, scores, status, and/or statistics related to UTI status, voiding (e.g., average number of voids per day, average number of urinations per day, average number of bathroom trips at night, average duration of bathroom trip, number of incontinence episodes per 24 hour period), times of scheduled and prompted voiding, stimulation therapy parameters (e.g., schedule and dose), medication therapy parameters (e.g., schedule and dose), sensed wetness at current time, number of pads used per day, average time between when a patient presses call button to ask for help to void and time of voiding, average number of times the patient presses call button per 24 hours (for bathroom reasons), (risk of) falls and mobility. BBA information can also include electronic bladder diary and quality of life scores, summary statistics, trend information, and threshold parameter definitions.

In embodiments, a PPM system component is a digital display configured to operate interactively using, for example, a touch screen, video, voice, RFID, and other sensing technology realized as a whiteboard 156 in a patient's room (or partially/fully as a smart-pad device). The whiteboard 156 displays updated information based upon a combination of the EHR and patient/caretaker/staff input and sensed data. The information displayed by the PPM solutions are customizable for hospital and patient. The digital displays show content organized into "data cells" (each having panels or fields that are populated by the PMP), each which can be moved, added or removed (with a user's preferences stored in the settings and permissions module 228). The whiteboard 156 displays data related to the patient, their treatment and staff, the day's activities or "plan for the day" (e.g. next scheduled bathroom trip as an assisted/unassisted event), meal time, provision of a Urostim treatment session for treatment for OAB), scheduled medications, etc.). Displayed data includes, for example, medically relevant information such as a patient's pain, discomfort, or anxiety level status may be displayed. A general risk score for falling, may be displayed and/or used to set permissions/restrictions for a patient such as whether they should be going to the bathroom independently or only assisted. A user can input data related to bathroom trips, such as "skipped", "did not void", "bladder", "bowel", "both".

The PMP whiteboard can show cardiac information such as heart rate and blood pressure which is obtained using a sensor worn or used by the patient. When a peripheral nerve stimulation device is used to module blood pressure, then an event such as a blood pressure change that exceed a defined range of normal can trigger a change in stimulation. The change can include stimulation that is started, stopped, or adjusted according to an algorithm of a treatment module 220. Alternatively, the event detection rule can cause patient or staff notification. When peripheral nerve stimulation treatment relates to disorders such as migraine, headache, tremor, hunger, eating (aspiration), digestion, disorder of the immune system, disorder of the cardiovascular system, disorder related to addiction, or other medical disorder or state that is unwanted with respect to patient health and wellness, then the data displayed and/or tracked by the PPM system is related to the disorder. In embodiments, the system provides treatment of unwanted conditions, improves clinical outcomes related to a disorder, provides lifestyle improvements (e.g. losing weight), or is used to treat or manage addictions such as smoking, drug/opioid abuse, and metabolic or psychiatric disorders.

In embodiments, a PMP system components includes digital displays that are realized to provide interfaces for a nurse station, a clinic management system, a whiteboard in the patient's room or a patient room door display that provides information (e.g., staff-assignments, pending or past-due events for the patient such as assisted ambulation for voiding, providing UroStim, pad/diaper changing times, and other BBA information) to hospital staff prior to entering a patient's room.

In an embodiment, the invention includes digital patient "whiteboards" which are used to display information and serve as a communication tool in Hospital/managed care/assisted living/retirement communities, The PMP and whiteboard 156 informs hospital staff and patients whether bathroom use requires assistance. The whiteboard 156 provides information in auditory and visual modalities allowing patient interaction, such as asking a question "Can I get up to go to the bathroom?". The PMP is configured to recognize the question and algorithmically answer using a rule that assesses a "fall risk score" and looks up the next scheduled bathroom event in the Scheduled activities module 204, to determine a delay time and respond to the patient "your fall risk is high, and it is suggested that you wait for assistance which will be coming in 12 minutes". The ability of a patient to view or ask about activities which are (or are not) recommended is also useful in patients who have memory or cognitive issues.

FIG. 11 shows a patient management display (PMD) 150 which is used, for example, at a nursing station to view and adjust patient data and care organized in the PMP system. In an embodiment, the PMD 150 shows data about a group of patients, dates/times of scheduled healthcare, staff who will provide various services, and notifications (alarms/alerts) related to the provision of care.

In embodiments, the PPM includes a Nurse Station Monitoring Display update the care team on round, stimulation, medication, and voiding activity schedules, and other information related to the patient current status and trends. A quick review can allow staff to review the status of multiple patients including their locations, upcoming scheduled activities, safety issues, bed status, etc. Care related to changing pads/diapers, the dry/wet status of a patient as well as duration for which a patient has been wet, etc. is displayed.

In this example, the first two columns indicate the patient room numbers and names. These columns are populated with information from the Patient module 202 of the PMP 200. When the PMD 150 is operated as part of a nurse station then clicking on the room number invokes a screen with information about the room (e.g., last time it was cleaned, any issues with equipment that have been reported, phone extension, etc.). Selecting any of the cells of the patient column invokes this screen. Selecting a field by mouse click or by tapping (or double tapping) on any of the displayed fields from the touch sensitive screen causes a subscreen to be displayed that has additional information about that field. For example, double tapping on the "UroStim" field|the "today's medical" portion of the screen opens up a screen that shows the schedule for the UroStim treatments, including times, durations, and stimulation parameters which will be used. The table shown in FIG. 11 will be discussed in relation to the PMP modules shown in FIG. 10, which support the provision of features and data associated with the table. The "Modules" are functional and relate to all software, hardware, algorithms, and operations that allow the module to fulfill its purpose. While the disclosed modules have been associated with particular functions, other modules may also provide similar functionality. The modules may be realized in a distributed manner and may exist within a computer network (e.g., hospital network), as well as devices that communicate with the network, and which in some embodiments provide nerve stimulation to a patient.

The "Next rounds" field is populated from scheduled activities module 204, and indicates when the patient is going to be visited by at least one staff member or attending physician. Similar fields can be populated in relation scheduled times for various points of contact between the patient and a nurse or other medical/support staff, including "next stim" or "next Med".

The "Toileting" field is populated from bladder bowel health management (BBHM) module 206, and indicates different types of toileting events associated with individualized toileting programs including scheduled (help the resident ambulate to the bathroom such as every 3-4 hours), prompted (periodically remind/ask the patient if there is a need for the bathroom, check wetness status), reinforcement (if a resident tends to visit the bathroom at a particular time day or night, they can be prompted to increase the habit). Prompting can occur in person or via an A/V message delivered in a patient's room by staff or a device such as a whiteboard or smartwatch. The "duration" provides a sense of how long the patient typically sits in the bathroom and can be in minutes or can be qualitative, such as quick (1-5 min), moderate (5-10), slow (10+). Under control of the BBHM module 206, medical staff are able to add additional delay time if the resident typically requires a significant amount of time to get to and from the toilet. Most common range for night-time bathroom trip—suggest scheduling a time—also if a bathroom trip occurs just prior to a scheduled trip then cancel this.

The "Provider" field is populated from staff-assignments module 208, which manages information on what staff is assigned to provide particular services to patients or which communicates with, or integrated into, the hospital's staff-assignment platform or EHR module 209 which is configured as the hospitals EHR or configured to communicate with the EHR to push and receive data.

The "Fall risk" field is populated from fall risk module 210, which stores patient scores or status with respect to falls. The fall risk module can assess information stored in the EHR 209 and also stores data about the history and description of falls to calculate a fall risk score, or this can be input by medical staff. The status is represented qualitatively (low, medium, high) or by a fall score ranging from 1 to 10 (highest risk). The score can be based upon data related to predicting risk of fall. This information can be summarized as a measure related to a history of falls, type of ambulatory aid, a dizziness score, gait issues, and mental status. Example of this are the Johns Hopkins, STRATIFY or Morse Scale which can result in a numeric score or a risk of high, medium, or low. Some risk tools already include "elimination" weighted sub-scores related to bowel and urine (incontinence, urgency or frequency, and the combination).

The out of bed "(OOB) status" field is populated from out of bed module 212 which can obtain information from bed sensors or a smart-bed system to indicate if a patient is laying down or sitting in the bed, motion sensors, IoT sensors that can sense patient location in the room, in the bathroom, on a smart-toilet, in a smart-chair or in a different location inside or outside of the medical facility. The algorithms of the OOB module 212 are configured to calculate a true or false result for "in bed" status, and also use additional time and sensor data to indicate activities such as sitting or sleeping.

The out of bed "(OOB) status" field can also operate in conjunction with the "Smart appliance" module 214 or other module of the PMP platform to provide information about various smart devices such as a smart bed which is configured with position, elevation, pressure, movement, and wetness sensors and associated processing circuitry. For example, the smart bed can determine if the patient is lying down or sitting up (position), in the bed (pressure), out of the bed, or has become incontinent (e.g. using a wetness sensor of the smart appliance module 214 configured to work with a bed). If the system detects changes in a patient's weight or position that indicates an intent to leave a bed, a visual or sonic alert signal may be triggered which provides an indication of the next voiding time.

The "Next Stim" field is populated from the stimulation treatment module 220. The stimulation treatment module stores the parameters of the treatment protocols such as the UroStim module, which operates to provide treatment of overactive bladder. The stimulation treatment module 220 has algorithms to provide patient reminders to provide stimulation to patients who are receiving stimulation such as from a wearable device, and can assess patient compliance in providing stimulation by assessing how often the patient's provide themselves with treatment. Failure to remain compliant can result in the PMP flagging the non-compliance and even automatically scheduling staff to provide "assisted treatment" for a selected number of days, weeks, or months.

The "UroStim" treatment module 222 operates to monitor and/or provide stimulation for the treatment of a pelvic floor disorder such as overactive bladder. It contains protocols and parameter values for providing and assessing treatment. In an embodiment, the Urostim module 222 is configured to allow a patient to control their stimulation therapy using the whiteboard as an interface and/or through voice services to start/stop therapy, increase/decrease amplitude of stimulation, and extend or reschedule a treatment session. In an embodiment, the whiteboard 156 simply serves to monitor the therapy that is provided by the patient by wirelessly establishing a communication session with the stimulation system, including the device 100, a custom remote or PDA 100 that controls the device 100, or an interface device such as a smartwatch 107 in the room that allows the user to provide stimulation or provides stimulation automatically. For example, the interface device 107 can be a device that transmits control signals, and/or power (or controls the transmission of power signals) to an implanted device to provide stimulation to the patent.

In an embodiment, the PMP includes digital displays that show data related to a history of at least one prior stimulation treatment, next stimulation treatment, number or schedule of stimulation treatments per day/week, stimulation treatment protocol parameters (duration, strength, etc), and expected patient activity during treatment (read, watch TV, etc).

The "Medical treatment" field is populated from medication treatment module 224 which stores the medications, doses, and schedules for providing these. Similar to the other modules of the PMP it can provide visual or sonic alert reminders (via the whiteboard or otherwise) related to scheduled medication to monitor and assist with medication compliance.

The "Provider" field is populated from the staff-assignments module 208, which is integrated into, or retrieves data from, the EHR system using the EHR module 209, and lists he staff member who is responsible for providing a service in the case that the patient does engage in an activity independently.

The "Med Diuretic" field is populated from the medication treatment module 224 and is calculated using an algorithm to determine the diuretic status. For example, the field can show a score that is based upon the number of medications the patient is taking which have diuretic effects. Additionally, by selecting this field a user can view all the medications of the patient that are contributing to this score.

The "# voids", "trending", "OAB Status", "Pads", "Wet/Dry", "UTI", fields are all populated using information managed by the bladder bowel health management (BBHM) module 206. The "# voids" field contains values such as the number of voids that have occurred since the patient awoke, the number of expected voids, and the number of voids that typically occur after the patient has gone to sleep. In the example shown in the figure, the Mr. Roberts has voided 4 times, out of an expected 9, and 1 of these will be nocturia, for which the patient will hopefully make a night-time trip to the bathroom. The expected number of voids can be computed from a moving average (or weighted average) of a prior period of for example, 1 day, 2-3 days, a week or month.

The "Trending" field is populated from the BBHM module 206 and the trending/statistics module 242 operating together and is calculated upon a history of bathroom frequency for the patient. For example, if the patient had a baseline of 10 trips to the bathroom and has recently averaged only 8 trips per day then the score would be +2 (a reduction in 2 trips). Alternatively, the trending field may be computed upon other data such as number of diaper changes due to incontinence, or other parameter. Selecting this field can show trend graph and summary statistics for tracked parameters such as diaper/pad usage, urge scores, frequency of bathroom trips, frequency of nigh-time trips, incontinence episodes per day, etc.

The "OAB" status field is populated to include a value of "none", "urge", "stress", and/or "mixed" as has been determined by the medical staff or otherwise. If the OAB status field is empty (indicated by "< >< >") or set to "None", then one or more of the rows or columns of the table such as the "toileting", "Duration", "next stim", "Med diuretic", "# voids", "trending", "Pads", "Wet/Dry", and "UTI" can be hidden. A status indicating no bladder issues can also cause cells of the whiteboard display of FIG. 12 to be hidden and alerts related to bathroom activity to be silenced.

The "pads" status field is populated by the BBHM module 206 working with the inventory module X, to include a value of reflecting the number of pads/diapers used by the patient. This can be input from the medical staff on a daily or weekly basis. For example, every time a box of pads is used and replaced with a new box, this box is scanned into the PMP system (e.g., using whiteboard sensor X) or is obtained from the inventory tracking module X.

The "wet/dry" status field is populated to include a value of reflecting the number of times a patient voids in a garment or bed in a manner that exceeds a criterion. For example, the criterion may be that the amount of voiding requires that the garment or bedsheets be replaced. The criterion can be assessed using sensors in the bed or garment (M. A. Ziai and John C. Batchelor Smart radio-frequency identification tag for diaper moisture detection. Health Technol Lett. 2015 February; 2(1): 18-21; TheraPee™; DryBuddy™) that measure moisture and a wet event occurs when moisture is detected or exceeds a defined limit such as 20%. The duration per week that the patient experiences moisture above a selected amount can be tracked, or the number of times per week that the patient is wet for longer than 1 hour, can be tracked by the BBHM module.

The "UTI" status field is populated to include a value of reflecting "none", "positive" or "negative" status, and/or "recurrent". If a patient is currently positive for UTI and also recurrent the filed can read "Pos; Recur". Selecting the field provides statistics on the history of UTI including duration, medication, severity, etc.

An additional field, not shown to avoid cluttering of the figure, is "incontinence" which is also populated from the BBHM module 206 and contains the number of incontinence episodes in the last 24 hours. Selecting this field can provide summary statistics and trend graphs.

The Alarms/Alerts status field is populated from Alarms/alerts module 226 and contains two levels of notification. For example, in the figure Mr. Roberts has 0 alarms and 2 alerts. The Alarms include events that require attention while alerts are worth noting but do not require any action. Alert events can escalate to alarm events when conditions are met. For example, an alert event may be if a patient has been "wet" (e.g. over 30%) for a duration (e.g., 1 hour) and this is defined to transition to an alarm event if this extends beyond a defined interval such as 2 hours. Alarm events can include, for example, determination that a patient with a high fall risk has gotten out of bed at night to use the bathroom. A patient who pressed the nurse call button more than a selected number of times over a selected interval such as 4 times in 1 hour, and a staff member has not responded. Reducing this type of occurrence can improve the patient experience and/or the statistics used to assess hospital care. If a patient currently has a UTI and has had a "wet" status for over a selected duration, that may result in an alarm or alert. Additionally, the alarm or alert can result in a display of a small circle indicator next to the alarm or alert value, with a color that can range from yellow to orange to red and which can be defined for various conditions associated with the alarm or alert.

Figure 12:
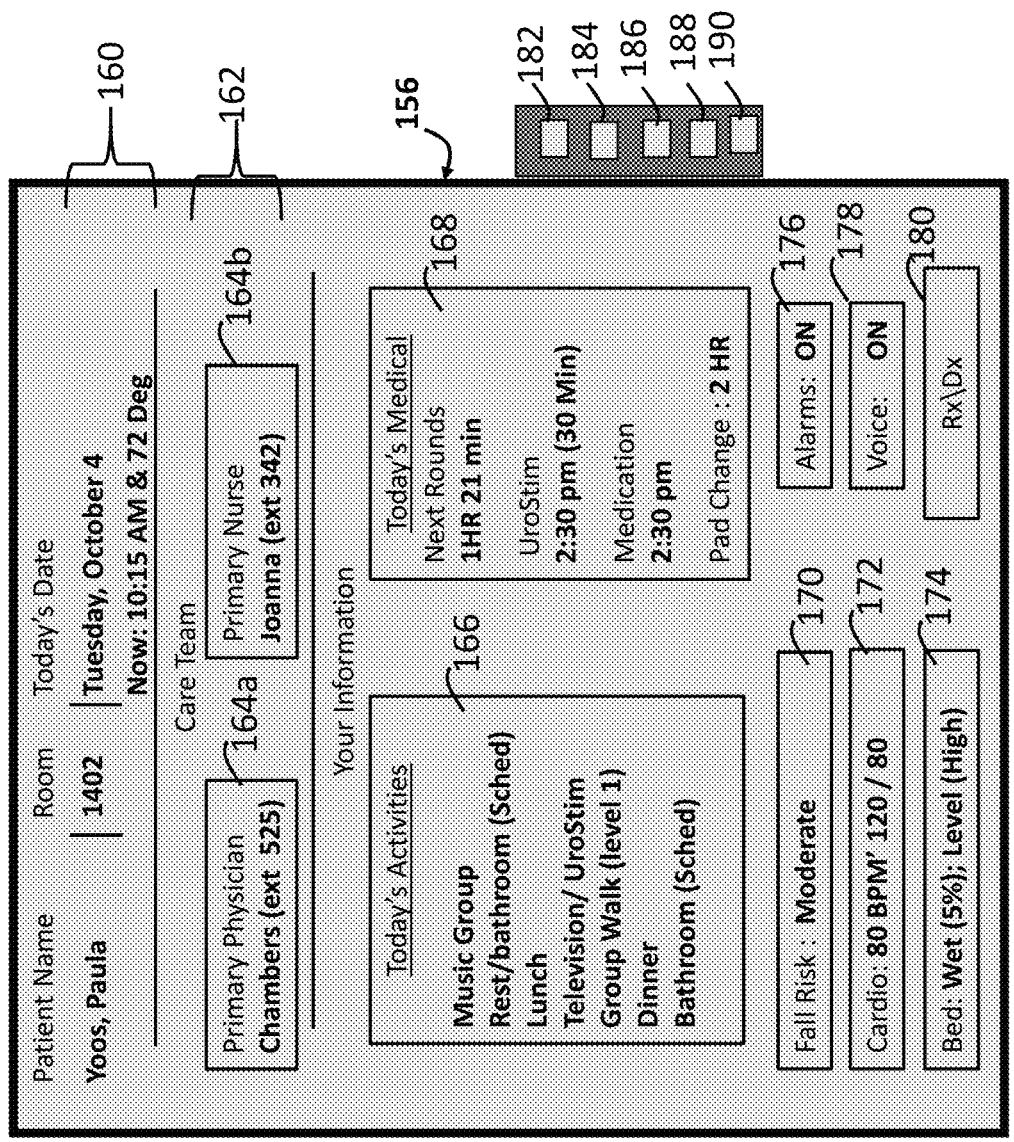
FIG. 12 shows an example of an interactive digital display of the patient management platform (PMP) system which is suitable as a whiteboard interface that may be located in a hospital room.

FIG. 12, shows an embodiment of an interactive whiteboard 156 which can be implemented as a smart-TV technology that provides display, as well as audio transducers (speakers) 182, microphone 184, video camera 186. Additionally, the whiteboard 156 has sensor/scanner technology 188 for identifying ID cards by IoT and RFID paradigms. One or more buttons 190, provide for manual input in addition to the touch sensitive display 192. A top portion 160 displays general information including patient's name from the patient module 202 (includes name, address, contact info, contact info for caretakers, etc), the room number, temperature (interior and/or exterior) obtained from the Patient Environment module 258 and the date/time from the Times & Durations module 260. Below that is the care team fields with values assigned from the staff assignment module 208.

The "Todays Activities" 166 and "Today's medical" 168 panels have fields that are populated from information from the scheduled activities module 204. The "Todays Activities" panel contains fields with activities listed in chronological order and can also be shown with approximate times. In the example shown the patient has 2 scheduled bathroom events which means that a staff member will be by to assist with ambulation to and from the toilet. The "Today's Medical" contains fields related to events at which the staff and patient interact, where the patient must perform an activity related to treatment, or where testing must occur. The scheduled times for next rounds, UroStim, and medication are shown. At the time of UroStim, the PMP may provide auditory and/or visual reminders to a patient to provide stimulation for treatment of a pelvic floor disorder such as stimulation of a nerve in the leg or foot. Additionally, using WIFI of the whiteboard, the PMP can turn on the stimulation when instructed by patient, show a timer that counts down the duration of the stimulation session, increase or decrease the amplitude of stimulation when instructed by the user, and prompt the user to provide data about symptoms. Alternatively, the whiteboard may simply remind the patient to provide the therapy. The whiteboard may be configured to periodically (e.g. 1× per day or week) communicate with the stimulation device 100 or other component 106 of the stimulation system to obtain data about usage, to update the historical record of use, and to assess compliance.

The "pad change" field of "Today's medical" panel 168 is populated from staff assignment module 208, and enables the patient to know when the next pad change is scheduled to occur. Selecting that field can permit a view of history of pad usage statistics and trends.

View permission and adjust field permission is managed by the permissions module 228 as a function of status, with options being patients, hospital support staff, pharmacists, doctors, etc. done In order to access a field, a user identifies themselves to the PMP system using their voice (with voice scan tech), their medical staff card, (using the sensor/scanner or camera), or otherwise as is well known. The PMP allows for hospital cards to be scanned, or otherwise identified, by the whiteboard to allow changes in parameter values or content that is displayed in the data cells.

The fall risk field 170 is populated by the fall risk module 210.

The "Cardio" field is populated from health status module 230, which is related to measuring and tracking variables related to assessing patient health. The cardiac data can be sensed by a wearable or "connected" device, or is manually entered by staff. The cardio field may include data related to heart rate, rhythm, blood pressure, peripheral blood gas (e.g., oxygen saturation), etc. When this is recorded by a wearable device, this measure can contribute to the fall risk score such as if the patient has low blood pressure. The blood pressure measurement can also be used to guide peripheral nerve stimulation treatment related to treatment of blood pressure and may alert a patient to provide stimulation treatment, or may assist with providing this by starting or stopping stimulation.

The "Bed" field 174 values related to moisture assessment "wet", and bed height "level" are populated from Smart appliance module 214. Moisture data sensed by sensors in the bed or in the patient's garments is displayed (e.g. 5%). The level of the bed may be displayed, which in this case is "high". It may be that after a certain time at night, the bed should be adjusted or automatically adjusts to a position which is "low" and which is set for the patient to enable the patient to easily get in and out of bed during the night to go to the bathroom. The time at which a patient is due to have an undergarment or incontinence pad changed is also noted.

When the PPM is operated with a hospital intranet which communicates with smart hospital beds technology, then the risk and frequency of patient falls can be decreased. When the fall risk score is above a selected amount then the status of the bed can be assessed and bed status information can be used to adjust patient treatment or alert hospital staff. For example, if a patient is known awake 1 or more time during the night then the bed level should be set to "low" or to a level that has been shown to facilitate the patient getting out of bed or returning to bed. Additionally, if the fall score is above a selected level then the smart bed technology may be restricted from allowing the patient to adjust the bed rail in order to leave the bed, or may alert the staff if the rail is placed in the down position during the night.

The "Alarms" field 176 is populated from Alarms/alerts module 226. Flashing visual alarms display Out Of Bed (OOB) status for the patient, while flashing bed alarm alerts notify staff of the room alarming, augmenting lights outside the room and nurse call alarms to reduce alarm fatigue in nurses and to encourage a healing environment.

The "Voice" field 178 is populated from voice services module 232 and can be toggled "On" or "Off" to permit voice services to be provided from the module.

The RX/DX field 180 is selected to allow the user to view, select, and adjust the value of parameters related to patient's care and can be used to adjust the treatment module 220, treatment protocol parameters and algorithms. RX is populated from Rx/Dx/Permissions module 238.

The speaker 182, microphone 184, camera (and camera "on" indicator) 186, are operated from A/V module 234 which also allows the whiteboard to receive and display various content. The A/V module 234 allows a user to allocate a portion of the screen to serve as a display for a TV, or video call between a remote user and a person in the patient's room.

The sensor/scanner 188 is operated in conjunction with a Sensing module 236 which allows the PMP's whiteboard 156 to serve as an interface that can scan inventory such as barcodes on a diaper or pad, stimulation pads, etc. This allows the PMP 200 to track use of medical disposables over time.

The whiteboard brightness automatically adjusts according to time (e.g. dimmer after a defined time associated with decreased activity or patient nap/sleep) and/or sound in the room, and/or light level. The brightness can be increased when a patient is scheduled to use the bathroom during evening hours and/or based upon the light level sensed in the room if it detects patient ambulation.

Figure 13:
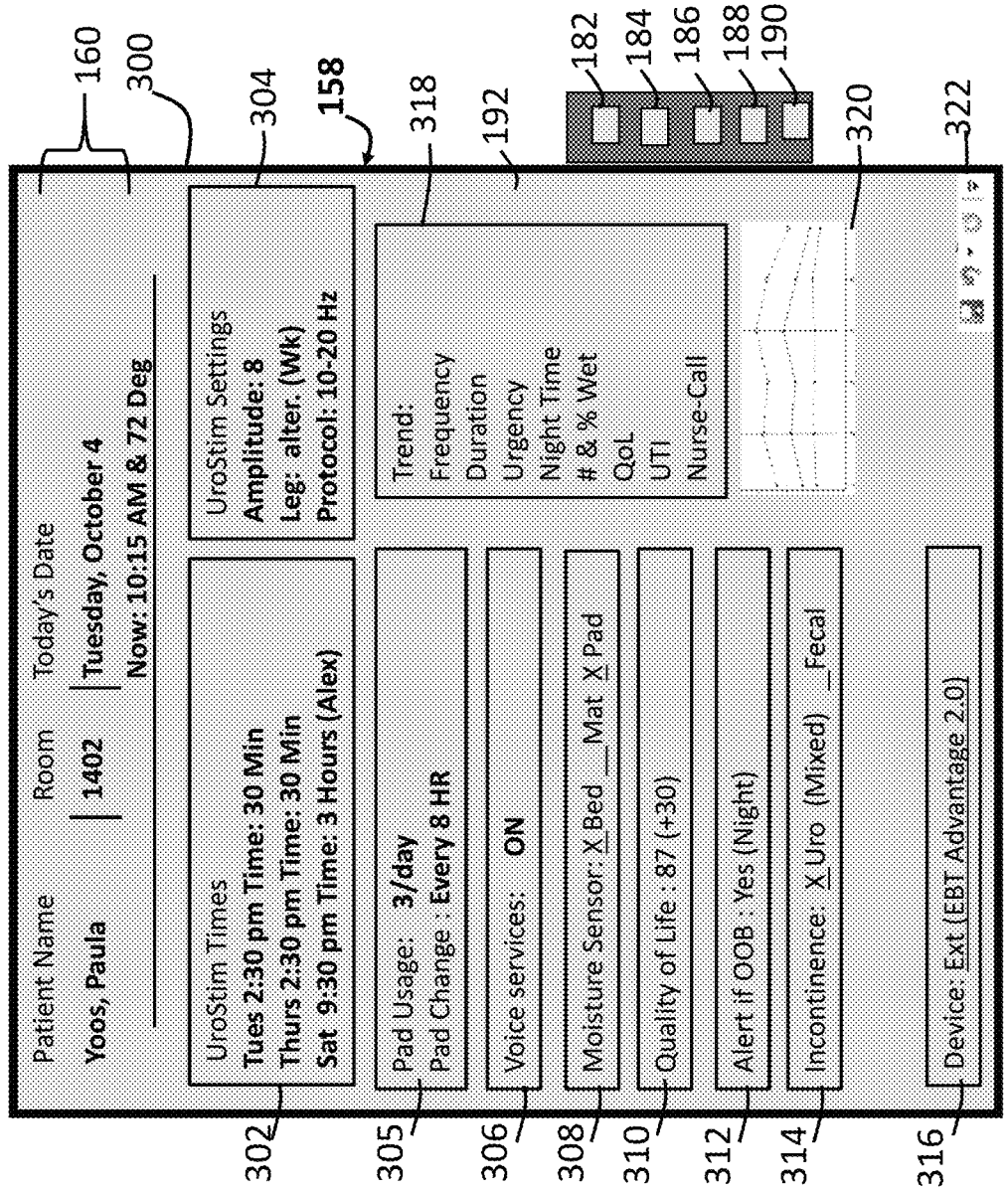
FIG. 13 shows an example of a sub-screen of an interactive digital display of the patient management platform (PMP) system which allows viewing of details related to stimulation treatment for a pelvic floor disorder such as overactive bladder.

FIG. 13 shows a bladder and bowel health sub-window screen 158 that is invoked by a user by selecting the Urostim field of the "todays medical" activities panel 168, or selecting a cell in the "next stim" column of the PMD display 150.

A top portion 160 displays general information including patient's name from the patient module 202 and the date/time from the Times & Durations module 260. Below that are Urostim times 302 corresponding to when stimulation sessions with a wearable provides therapy for OAB symptoms, and settings panel 304 which are both defined in the Urostim module 222. The urostim times indicate that on the Saturday session will be assisted by a staff member, "Alex", as defined by the staff assignment module 208.

The "Pad" panel 305 contains fields related to how many pads are used per day and the schedule for changing these, as obtained from the BBHM module 206.

The "Voice services" field 306 is toggled to "On" as indicated by the voice services module 232 indicating that the PMP is configured to accept voice commands from the patient or caregivers in accordance with defined permissions 228.

The "moisture sensor" panel 308 contains fields related to whether a moisture sensor is turned on in a smart-bed, on an accessory mat used with a bed/mattress, or implemented within a pad/undergarment as indicated by the smart appliance 214 or sensing 236 module.

The "Quality of Life" field 310 displays 87 (+30), where the first number is the current score and the second number is a change from at least one prior period that is serving as baseline. These values are populated either from the algorithms of the survey module 240, or obtained from the EHR module 209.

The "Alert if OOB" panel 312 contains fields related to whether an alarm or alert should be provided if the patient is out of bed as determined by the OOB module 212, and the parameter settings of the alarms/alerts module 226, which are set enable alerting to occur if the OOB event occurs during a period defined as "night". The OOB module can obtain data from sensors of the sensing module 236 that track patient movement and location, such as toilet sensors that allow automatic recording of how long a patient spends on the toilet or mat sensors that can be configured to detect a patient walking in the room.

The "Incontinence" panel 314 contains fields that qualify if incontinence is present and whether it is bladder (with further qualifications at least one of of stress, urge, mixed, nocturia, enuresis, acute, stable, worsening, improving), bowel, or both, as indicated in the BBHM module 206. The status of improving or worsening can be calculated by evaluating trend data in relation to criteria defined for improving or worsening, respectively.

The "device" panel 316 contains fields related to devices registered to the patient and room so that the PMP can communicate with the devices appropriately. For example, in the figure an external stimulator model Advantage 2.0 (EBT Medical) has been registered. This allows the PMP to communicate and or control the device to manage or monitor electrical therapy such as that related to treatment of overactive bladder. The device is able to communicate with, and provide control signals to, external devices, implanted devices, external devices that control implantable devices, etc.

The "trend" panel 318 contains fields that invoke graphs and screen that display trends for various measurements related to bladder and bowel health such as frequency, duration (average duration of bathroom trips), urgency, night time events (nocturia/bedwetting), the number of wet events that occur during the day, measured amount and duration of wetness, quality of life (QOL) calculated upon survey questions and sensed data, urinary tract infection presence/absence, and nurse calls, with subsets related to bladder/bowel issues. Selecting any of the fields in the trend panel will cause the trend graph 320 to change the information displayed.

The screen 158 also has touch menu controls 322 for saving parameter values and selections, reverting to prior settings, exiting the screen, and other menu options.

Additional modules of the example PMP 200 shown FIG. 11, which were not disclosed in relation to fields illustrated in FIG. 10, 12 or 13 will now be disclosed.

The "pain" module 216 is configured for obtaining and storing information about a patient's pain level and type. The pain information can be obtained by the PMP prompting the patient about their pain, such as "rate your pain between 1 and 10" or "has your pain increased, decreased, or stayed the same since last time we checked"? Alternatively, the medical staff can input this information into the EHR to which the pain module 216 has access. A wearable neurostimulator 100*a* may have software which queries the patient about their pain and this data is then transmitted to the PMP whiteboard.

The "movement" module 218 records information about patient movement including walking, speed, and/or gain. Movement measures may be obtained from wearable sensors X, sensors provided on a wearable device X, or may be scored by medical staff in input into the PMP. When movement scores are computed from data sensed during sleep by sensors of the bed or in a wearable device then these data or scores are transmitted to the movement module 218. The movement module 218 is configured to score raw data and summary scores, and to also store and present trend data related to movement. When the PMP is configure to assess movement related to tremor or rigidity, then electrical or other stimulation/treatment can be algorithmically adjusted based upon this assessment.

The "Survey" module 240 prompts patient with questions related to the provision of treatment such as the treatment of bladder and bowel disorders or activities. The survey module may ask a patient if they made it to the bathroom without leaking and obtain a response, or may present survey questions to a patient on a tablet computer or other accessory of the system X. The survey module 240 has algorithms for presenting and assessing answers to questions. For example, algorithms contain questions, parameter values and data related to what questions to ask a patient (e.g., logic trees that bring up subsequent questions based upon answers to earlier questions) and timing or contingent conditions that cause questions to be asked, as well as rules for how to score the questions to create various metrics. For example, quality-of-life (Qol) algorithms are used to process data related to quality of life surveys, to create quality of life scores. In an embodiment the survey questions relate to an assessment of a patient's health in relation to a bowel or bladder disorder.

The "Trend/Statistics" module 242 performs trend, summary, and statistical analysis on patient data and displays these data for default or user selected intervals.

The "database/mapping" module 244 relates to storage and retrieval of data used by the PMP. It interfaces with the hospital or clinic EHR to operate upon EHR data to present it in a format used by the PMP. Stored data may be mapped to units or names that are easier for a patient or medical staff to understand. For example, a quality of life measure of 80% may be converted into "good", while a measure below 40 may be mapped to "poor" when it is presented to a user by whiteboard or otherwise. Healthcare acronyms used in the EHR can be mapped to colloquial terms or ignored, The "Nurse Call" module 246 records and tracks when and how many nurse calls (call bell, call light, etc.) are requested by a patient, the reason for the call, and the delay between the time of the nurse call request and response times. Phones, pagers, bed controls, moisture/toilet sensors, and badges are among the electronic devices that may send messages to this module. The module may assign a particular nurse to answer a bell request. More typically staff at a nurses' station, will talk with the patient via an intercom system and assign the task. Peak call bell use occurs at change of shift and around meal times and top reasons for calling are toileting, positioning, and pain management. The BBHM module may decrease the load related to toileting by scheduling meal time of a patient in relation to how long after the meal the patient may typically void. The nurse call module can be implemented to communicate with, or be integrated with Rauland's Responder® integrated health care communications systems or Responder NET (Primary Systems) platforms. Rather than pressing a call button, data can be sensed using voice services technology.

The "Devices/Sensors" module 248, associates a sensing or stimulation device to a particular patient. For example, if a stimulation device is shared in several rooms the module can communicate with the device and associate a treatment delivered by the device to a particular patient in that patient's room. It also modifies the stimulation protocol implemented by the device according to the patient who is in the room, or can identify the patient via a smart-bracelet worn by the patient that is part of the devices/sensors module 248. Instead of using a smartphone or remote controller, the PPM (e.g., via the whiteboard) can be "paired" with the stimulation device so that it may store its ID and then control it and/or display such data as duration of stimulation, time left, amplitude and stimulation protocol parameter values, impedance values, number of uses since stimulation pads were replaced, etc. (Pairing/control module)

The "Communication" module 250 provides communication between the PMP, devices used by the patient, entities such as insurance companies, doctor offices, mobile devices of care providers, family members, and medical staff.

The "Inventory tracking" module 252 tracks disposables or other assets used by the patient and contains lists that track serial numbers, RFID, IoT or other type of product Intensification and can map to products and disposables. The inventory tracking module can work in conjunction with the scanner module to track disposables (or boxes that contain 1 or more disposables) that are scanned into the PMP by medical staff when they are used, as they are thrown into the trash (by appropriately located sensors), or otherwise. In an embodiment, the whiteboard is incorporated as the front of a smart-storage cabinet having inventory that can be tracked by RFID or other technology and the inventory tracks items as they disappear from the inventory and fail to remain present. When used in a hospital setting the inventory tracking module may notify staff when a particular supply is low, and when used in a home or assisted living environment may be used with the shopping cart module to order replacement supplies when it detects a selected minimum level. In an alternative embodiment, smart storage cabinet may measure what is on its shelf by video sensors that measure height or volume, mats that measure weight.

The "shopping cart" module 254 associates a patient, caregiver, or user with a particular credit card, or account number or other means for purchasing goods using electronic orders. It may add items to a list of hospital charges or may otherwise provide the ability for charging or payment of one party to a second party.

The "Interactive" module 256 catalogues information related to the presentation of information to the patient, via whiteboard or other devices that interact with a patient. The interactive module can control interactive multimedia technologies such as the Smartboard 7000 (Smart Technologies ULC), or other touchscreen technologies (e.g., QB75H-TR—Edge-Lit 4K UHD LED Interactive Display, by Samsung) having built in wireless communication and multiple ports for connection to other equipment. The interactive module 256 interacts with the language module 262 to adjust the language implemented by the PMP when interacting with a patient, doctor, or staff member.

Generating Reports

The "Reports" module 264 allows the PMP to create reports that can be used in assessment of hospital performance. With respect to promotion of BBHM, the module can report on hospital wide occurrence of UTIs, falls related to bathroom activity, average duration that patient's remain wet above a selected amount (when sensors are used), average number of wet episodes, the compliance of providing of electrical stimulation for the treatment of a pelvic floor disorder such as OAB, the prevalence of restless leg syndrome, number of patients who get up more than 1× or 2× per night to void etc. The Reports module 264 also permits the ability for each patient to be tracked both before (baseline) and after the provision of electrical therapy for treatment of OAB, to report on improvement and sustained improvement (maintenance).

The PMP connects to the hospital intranet or similar protected health information (PHI) computer networks. The PMP accesses databases such as an EHR system, and system operating to provide "nurse-call" features, staff-assignments, and smart-bed technology. Additionally, the PPM can integrates with in-room devices such as a smart-bed using wireless communication protocols. The PPM monitors use of disposables, including pads, diapers, stimulation device, pads, and protocols (used to provide electrotherapy). The monitoring of disposables can occur using RFID technology where the disposable is scanned by a sensor 188 such as an RFID, barcode, NFC/Bluetooth, or IOT enabled sensor of the whiteboard (e.g. the DS9808-R or RFD8500i). Using a voice service the patient or staff can also verbally inform the PMP about a diaper change, and the interaction occurs via a microphone 184, speaker 182, and voice service subroutines that may operate within the hospital or provided by the voice service module 232.

The "Billing/third party" module 264 allows the PMP to operate to perform billing and payment operations related to costs and charges incurred during the provision of patient care including for example, use of disposables, medications, services, and/or the provision of therapy such as peripheral nerve stimulation therapy (e.g., to improve symptoms related to pelvic health). This module also provides communication with third parties such as private payors, insurance entities, and other healthcare service providers.

The PMP control module 268 includes the software instructions, processors, memory, power, communication, and other hardware that may be realized in a distributed manner using computer servers, cloud services, and medical devices to coordinate the operation of the modules of the PMP system 200.

Figure 14:
FIG. 14 shows an example of a patient management platform (PMP) system being implemented in a patient's hospital room to provide benefits including management stimulation such as for treatment of overactive bladder.

FIG. 14 shows an example of a patient management platform (PMP) system being implemented in a patient's hospital room 330 to provide benefits including management stimulation such as for treatment of overactive bladder. The figures shows a smart-bed 332 having a mattress moisture sensor pad 334 for measuring incontinence, a set of controls 336 for allowing control of bed features (e.g., height) a well as for electronically controlling the position of the retaining barrier 338. A smart-floor-mat 340 is shown which can detect when the patient is ambulatory and which communicates with a PMP component such as the whiteboard 156 through wired or wireless means. The patient may interact with the PMP using the whiteboard 156, or using a voice service enabled clock 158. A wearable neurostimulation device 100a is shown having a display 160 that may flash or provide other signaling related to scheduled stimulation sessions or other events. The nurse bell button 162 may be comprised of more than 1 button to indicate urgency or type of need and it communicates with the PMP to track usage and other information.

References and citations to other documents, such as patents, patent applications, patent publications, journals, books, papers, have been made throughout this disclosure. All such documents are hereby incorporated herein by reference in their entirety for all purposes.

This application contains section headings that are provided for organizational reasons only and are not meant to limit the invention in any manner.

EQUIVALENTS

The invention may be embodied in other specific forms without departing from the spirit or essential characteristics thereof. The foregoing embodiments are therefore to be considered in all respects illustrative rather than limiting on the invention described herein.

Certain nerve targets which are associated with certain disorders can be used to treat other disorders disclosed herein as well.

The various steps disclosed herein (such as, for non-limiting example, logic that performs a function or process) may be described as data and/or instructions embodied in various computer-readable media, in terms of their behavioral, and/or other characteristics. The logic and methods described herein may comprise, according to various embodiments of the invention, software, hardware, or a combination of software and hardware.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. When the word "or" is used about a list of two or more items, then that word covers the following interpretations of the word: any of the items, all of the items, and any combination of the items in the list.

The above descriptions of illustrated embodiments of the system, methods, or devices are not intended to be exhaustive or to be limited to the precise form disclosed. While specific embodiments of, and examples for, the system, methods, or devices are described herein for illustrative purposes, various equivalent modifications are possible within the scope of the system, methods, or devices, as those skilled in the relevant art will recognize. The teachings of the system, methods, or devices provided herein can be applied to other processing systems, methods, or devices, not only for the systems, methods, or devices described.

In general, in any claims, the terms used should not be construed to limit the system, methods, or devices to the specific embodiments disclosed in the specification and the claims, but should be construed to include all systems that operate under the claims.

While preferred embodiments of the present invention have been shown and described herein, it will be obvious to those skilled in the art that such embodiments are provided by way of example only. Numerous variations, changes, and substitutions will now occur to those skilled in the art without departing from the invention.

What is claimed is:

1. A nerve treatment system for delivering electrical signals to a target nerve comprising:
   (a) a singular housing having a base adapted to be mounted contiguous an external skin layer of a patient;
   (b) a displaceable electrical stimulator positioned within said singular housing for emitting an electrical signal to said target nerve, said displaceable electrical stimulator positioned within said housing for percutaneous displacement of said displaceable electrical stimulator to a predetermined selectable depth beneath the external skin layer of the patient defining at least two differing first and second selected depths;
   (c) a connector conduit unit located within said singular housing and adapted to connect the displaceable electrical stimulator to a signal generator of a neurostimulator through an electrical port formed in a wall of said singular housing; and,
   (d) a percutaneous stimulator displacement mechanism including a linearly adjustable stop block adapted to be releasably coupled to said displaceable electrical stimulator in at least two differing first and second positions corresponding to at least one of said two differing first and second selected depths for displacing said displaceable electrical stimulator to said predetermined selectable depth beneath the external skin layer of the patient to a location adjacent to or contiguous with a target nerve to be treated, said percutaneous stimulator displacement mechanism having said linearly adjustable stop block displaceably mounted on the displaceable electrical stimulator for limiting said selectable depth to which said displaceable electrical stimulator is able to be displaced beneath the external skin layer of the patient and where said percutaneous stimulator displacement mechanism includes:

(a) a spring biased member containing a spring member coupled to said displaceable electrical stimulator for maintaining said displaceable stimulator within the confines of said singular housing in an un-deployed state and release of said displaceable electrical stimulator to be displaced percutaneously to a deployed state; and, (b) a displaceable locking member for bearing against said spring biased member to maintain said displaceable stimulator in said un-deployed state and releasing said displaceable electrical stimulator in a deployed state.

2. The system as recited in claim 1, wherein the base has an electrically conductive region.

3. The system as recited in claim 1, further including where said neurostimulator is electrically coupled to said electrical generator and to said displaceable electrical stimulator through the connector conduit unit adapted to transmit electrical stimulation signals from the electrical generator to said displaceable electrical stimulator.

4. The system as recited in claim 1 where said singular housing includes a housing displaceable stimulator guide passage for receiving said displaceable electrical stimulator, said housing displaceable stimulator guide passage in linear alignment with a base guide passage for providing a guide path for said displaceable electrical stimulator.

5. The system as recited in claim 4 where said housing displaceable stimulator guide passage and said base guide passage are aligned each with respect to the other and extend in a direction substantially perpendicular to a planar section of a top surface of said base.

6. The system as recited in claim 4 where said housing stimulator guide passage and said base guide passage are aligned each with respect to the other and form a predetermined acute angle with respect to a planar section of a top surface of said base.

7. The system as recited in claim 4 where said percutaneous displaceable electrical stimulator is slideably displaceable within said housing displaceable guide passage and said base guide passage.

8. The system as recited in claim 1 where said displaceable electrical stimulator is an electrically conductive needle.

9. The system as recited in claim 1 where said singular housing includes said electrical housing port formed through a sidewall of said singular housing for receipt of said connector conduit unit, said connector conduit unit electrically connected on opposing ends thereof to said electrical housing port and said neurostimulator.

10. The system as recited in claim 9 where said connector conduit unit includes a first electrically internal flexible conductive conduit which is connected on opposing ends thereof respectively to said displaceable electrical stimulator and said electrical housing port.

11. The system as recited in claim 10 where said connector conduit unit includes a second electrically internal conductive conduit connected on respective opposing ends to said electrical housing port and an electrically conductive region of said base, said base being contiguous the external skin layer of the patient, whereby said electrically conductive region of said base serves as a transdermal electrical stimulation electrode.

12. The system as recited in claim 1 where said displaceable locking member includes at least one displaceable pinch tab mounted to said singular housing which is fixed to said spring biased member in said un-deployed state and released from said displaceable electrical stimulator in said deployed state.

13. The system as recited in claim 1 where said linearly adjustable stop block contacts an upper surface of said singular housing when said displaceable electrical stimulator has reached at least one of the first and second selected depths beneath the external skin layer of the patient.

14. The system of claim 1, further including a wearable garment housing the neurostimulator and adapted for securement to the patients leg for providing stimulation to at least a portion of a leg of the patient.

15. The system of claim 14 wherein the neurostimulator is configured to provide electrical nerve stimulation wherein the stimulation is at least one of percutaneous or transcutaneous nerve stimulation.

16. The system of claim 1 wherein the selectable depth is between 0.5 and 1 cm below the skin surface.

17. The system of claim 1 wherein the selectable depth is between 0.5 and 2 cm below the skin surface.

18. A nerve treatment system for delivering electrical signals to a target nerve comprising:

(a) a singular housing having a base adapted to be mounted contiguous an external skin layer of a patient;

(b) a displaceable electrical stimulator for emitting an electrical signal to said target nerve, said displaceable electrical stimulator positioned within said singular housing for percutaneous displacement of said displaceable electrical stimulator to a selectable depth beneath the external skin layer of the patient;

(c) a connector conduit unit located within said singular housing and adapted to connect the displaceable electrical stimulator to a signal generator of a neurostimulator through an electrical port formed in a wall of said singular housing; and, (d) a percutaneous stimulator displacement mechanism for displacing said displaceable electrical stimulator to said selectable depth beneath the external skin layer of the patient to a location adjacent to or contiguous with a target nerve to be treated, said percutaneous stimulator displacement mechanism defining a push button mounted on said singular housing and in contact with said displaceable electrical stimulator for displacement of said displaceable electrical stimulator to said selectable depth when a displacement force is applied to said push button, said push button being a deformable button which contacts and displaces said electrical stimulator when a displacement force is applied to said deformable push button.

19. The system as recited in claim 18 where said deformable button member is slidably displaced within said singular housing to a length equal to said selectable depth.

20. The system as recited in claim 19 where the length of said singular housing is equal to the selectable depth.

* * * * *